US008586553B2

(12) United States Patent
Awasthi et al.

(10) Patent No.: US 8,586,553 B2
(45) Date of Patent: Nov. 19, 2013

(54) THERAPIES FOR CANCER USING RLIP76

(75) Inventors: Sanjay Awasthi, Arlington, TX (US);
Sharad S. Singhal, Arlington, TX (US);
Sushma Yadav, Arlington, TX (US)

(73) Assignee: Board of Regents, The University of Texas System, Austin, TX (US)

( * ) Notice: Subject to any disclaimer, the term of this patent is extended or adjusted under 35 U.S.C. 154(b) by 775 days.

(21) Appl. No.: 12/055,138

(22) Filed: Mar. 25, 2008

(65) Prior Publication Data

US 2010/0183702 A1 Jul. 22, 2010

Related U.S. Application Data

(63) Continuation of application No. 11/264,910, filed on Nov. 2, 2005, now abandoned, and a continuation-in-part of application No. 10/714,506, filed on Nov. 13, 2003, now abandoned, application No. 12/055,138, which is a continuation-in-part of application No. 10/713,578, filed on Nov. 13, 2003, now abandoned.

(60) Provisional application No. 60/425,917, filed on Nov. 13, 2002, provisional application No. 60/425,814, filed on Nov. 13, 2002.

(51) Int. Cl.
*C12N 15/113* (2010.01)

(52) U.S. Cl.
USPC ........................................................ 514/44 A

(58) Field of Classification Search
None
See application file for complete search history.

(56) References Cited

U.S. PATENT DOCUMENTS

| | | | |
|---|---|---|---|
| 6,120,198 A | 9/2000 | Sawano et al. | |
| 6,750,015 B2 | 6/2004 | Horwitz et al. | |
| 7,611,839 B2 * | 11/2009 | Twine et al. | 435/6.14 |
| 8,163,692 B2 | 4/2012 | Awasthi et al. | |
| 2002/0119156 A1 | 8/2002 | Chen et al. | |
| 2003/0138793 A1 | 7/2003 | Su et al. | |
| 2004/0156853 A1 | 8/2004 | Awasthi et al. | |
| 2005/0123594 A1 | 6/2005 | Awasthi et al. | |
| 2005/0208054 A1 | 9/2005 | Czech et al. | |
| 2006/0182749 A1 | 8/2006 | Awasthi et al. | |
| 2008/0279919 A1 | 11/2008 | Awasthi et al. | |
| 2011/0020432 A1 | 1/2011 | Cunningham | |
| 2011/0020433 A1 | 1/2011 | Cunningham | |

FOREIGN PATENT DOCUMENTS

WO  2007/127439 A2  11/2007

OTHER PUBLICATIONS

Singhal et al (Biochemical Pharmacology, 2005, 70:481-488).*
Singhal et al (Biochemical Pharmacology, 2009, 77:1074-1083).*
Singhal et al (Cancer Research, 2006, 66:2354-2360).*
Singhal et al (Cancer Research, 2007, 67:4382-4389).*
Kumar et al (Advanced Drug Delivery Reviews, 2007, 59:87-100).*
Devi (Cancer Gene Therapy, 2006, 13:819-829).*
Ponnappa et al (Journal of Pharmacology and Experimental Therapeutics, 2001, 297:1129-1136).*
Sioud et al (Biocehmical and Biophysical Research Communications, 2003, 312:1220-1225).*
Dainiak N., "Hematologic consequences of exposure to ionizing radiation", *Exp. Hematol.*, 30(6):513-528 (2002).
US NRC published a fact sheet on biological effects of radiation (Dec. 2004, 9 pages).
Wagner et al., "Treatment of radiation exposure and contamination", *Radiographics.*, 14(2):387-396 (1994).
Awasthi, et al. "RLIP76 Is a Major Determinant of Radiation Sensitivity," *Cancer Research*, 65:6022-6028 (2005).
American Type Culture Collection (Tumor Cell Lines, 2001).
Awasthi et al., Proceedings of the American Association for Cancer Research, vol. 43, Mar. 2002, (Abstract).
Awasthi et al., "A Novel Mechanism of Drug Resistance in Epilepsy", Blood Brain Barrier Conference at Cleveland Clinic Foundation, Cleveland, OH, Nov. 2-3, 2004, (Abstract).
Awasthi et al., "Anti-RLIP76 Antibodies Induce Apoptosis and Enhance Doxorubicin Cytotoxicity in Lung Cancer Cells", American Association for Cancer Research, 92nd Annual Meeting, New Orleans, LA, Proceedings: 42, Parch 24-28, 2001, (Abstract 1507).
Awasthi et al., "Anti-RLIP76 Antibodies Induce Apoptosis in Lung Cancer Cells and Display Marked Synergy with Doxorubicin", American Association for Cancer Research, 93rd Annual Meeting, San Francisco, CA; Proceedings: 43, Apr. 6-10, 2002, (Abstract 4717).
Awasthi et al., "ATP-Dependent Colchicine Transport by Human Erythrocyte Glutathione Conjugate Transporter", Toxicology and Applied Pharmacology, vol. 155, Issue 3, 1999, pp. 215-226.
Awasthi et al., "ATP-Dependent Human Erythrocyte Glutathione-Conjugate Transporter. I. Purification, Photoaffinity Labeling, and Kinetic Characteristics of ATPase Activity", Biochemistry, vol. 37, Issue 15, 1998, pp. 5231-5238.
Awasthi et al., "ATP-Dependent Human Erythrocyte Glutathione-Conjugate Transporter. II. Functional Reconstitution of Transport Activity", Biochemistry, vol. 37, Issue 15, 1998, pp. 5239-5248.
Awasthi et al., "Functional Reassembly of ATP-Dependent Xenobiotic Transport by the N- and C-Terminal Domains of RLIP76 and Identification of ATP Binding Sequences", Biochemistry, vol. 40, Issue 13, 2001, pp. 4159-4168.
Awasthi et al., "Novel Function of Human RLIP76: ATP-Dependent Transport of Glutathione Conjugates and Doxorubicin", Biochemistry, vol. 39, Issue 31, 2000, pp. 9327-9334.

(Continued)

*Primary Examiner* — Laura B Goddard
(74) *Attorney, Agent, or Firm* — Kilpatrick Townsend and Stockton LLP

(57) ABSTRACT

The present invention is a composition identified as a region of ralA binding protein 1, wherein the region neighbors a membrane-associated portion of the ralA binding protein 1, reduces transport activity and membrane association of the ralA binding protein 1 and kills cells undergoing uncontrolled cell growth in a subject that has cells undergoing uncontrolled cell growth. The region is used to generate medicines that kill malignant cells and tumorigenic cells. Medicines may be in the form of antibodies, si-RNA and small molecules that recognize the region.

11 Claims, 4 Drawing Sheets

(56) References Cited

OTHER PUBLICATIONS

Awasthi et al., "RALPB1 is a major determinant of radiation sensitivity and glutathione-Conjugate transport", American Association for Cancer Research, 95th Annual Meeting, Orlando, FL, Mar. 27-31, 2004, (Abstract).

Awasthi et al., "RLIP76 and Cancer", Clinical Cancer Research, vol. 14, No. 14, 2008, pp. 4372-4377.

Awasthi et al., "RLIP76 Mediates Doxorubicin Transport and Resistance in Lung Cancer", 18th Annual Meeting of the International Society for Biological Therapy of Cancer (ISBTCI) Bethesda, MD, Oct. 30-Nov. 2, 2003, (Abstract).

Awasthi et al., "RLIP76, a non-ABC transporter, and drug resistance in epilepsy", BMC Neuroscience, vol. 6, 2005, pp. 61-71.

Awasthi et al., "RLIP76, a Novel Transporter Catalyzing ATP-Dependent Efflux of Xenobiotics", Drug Metabolism and Disposition, vol. 30, Issue 12, 2002, pp. 1300-1310.

Awasthi et al., "Role of RLIP76 in lung cancer doxorubicin resistance: II. Doxorubicin transport in lung cancer by RLIP76", International Journal of Oncology, vol. 22, No. 4, 2003, pp. 713-720.

Awasthi et al., "Role of RLIP76 in lung cancer doxorubicin resistance: III. Anti-RLIP76 antibodies trigger apoptosis in lung cancer cells and synergistically increase doxorubicin cytotoxicity", International Journal of Oncology, vol. 22, No. 4, 2003, pp. 721-732.

Awasthi et al., "Targeting Multiple Signaling Pathways with RLIP76, Gordon Conference on Molecular Therapeutics of Cancer", Colby Sawyer College, New London New Hampshire, Jul. 20, 2005, (Abstract).

Awasthi et al., "Tyrphostin and Genistein Inhibit ATPase and transport activity of RLIP76 and increase doxorubicin toxicity in lung cancer cells", American Association of Cancer Research, 94th Annual Meeting, Washington, D.C., Jul. 11-14, 2003, (Abstract).

Awasthi et al., "Transport of glutathione conjugates and chemotherapeutic drugs by RLIP76 (RALBP1): A novel link between G-protein and tyrosine kinase signaling and drug resistance", International Journal of Cancer, vol. 106, Issue 5, 2003, pp. 635-646.

Baglia et al., "A Binding Site for Thrombin in the Apple 1 Domain of Factor XI", The Journal of Biological Chemistry, vol. 271, No. 7, 1996, pp. 3652-3658.

Black et al., "Effects of Dietary Constituents on Ultraviolet Light-mediated Carcinogenesis", Cancer Research, vol. 38, No. 5, May 1978, pp. 1384-1387.

Cheng et al., "Accelerated Metabolism and Exclusion of 4-Hydroxynonenal through Induction of RLIP76 and hGST5.8 is an Early Adaptive Response of Cells to Heat and Oxidative Stress", The Journal of Biological Chemistry, vol. 276, No. 44, 2001, pp. 41213-41223.

Dermer et al., "Another Anniversary for the War on Cancer", Biotechnology vol. 12 No. 3, Mar. 12, 1994, 4 Pages.

Drake, "RALBP1 in Stress Resistance", The University of Texas at Arlington in Partial Fulfillment of the Requirements for the Degree of Doctor of Philosophy, Retrieved from the Internet: <https://dspace.uta.edu/bitstream/handle/10106/912/umi-uta-1996.pdf?sequence=1> on Apr. 8, 2013, Dec. 2007, 129 pages.

Felnerova et al., "Liposomes and Virosomes as Delivery Systems for Antigens, Nucleic Acids and Drugs", Current Opinion in Biotechnology, vol. 15, 2004, pp. 518-529.

Freshney, "Culture of Animal Cells", A Manual of Basic Technique, 1983, 4 pages.

Iyer et al., "Effects of ionizing radiation in targeted and nontargeted cells", Archives of Biochemistry and Biophysics, vol. 376, No. 1, 2000, pp. 14-25.

Leenaars et al., "The Production of Polyclonal Antibodies in Laboratory Animals", ATLA, vol. 27, 1999, pp. 79-102.

Margutti et al., "Autoantibodies to the C-terminal subunit of RLIP76 induce oxidative stress and endothelial cell apoptosis in immune-mediated vascular diseases and atherosclerosis", Blood, vol. 111, No. 9, Nov. 2007, pp. 4559-4570.

Sause, "The Role of Radiotherapy in Non-Small Cell Lung Cancer", Chest, vol. 116 (Supplement), Issue 3, 1999, pp. 504S-508S.

Sharma et al., "RLIP76 Is the Major ATP-Dependent Transporter of Glutathione-Conjugates and Doxorubicin in Human Erythrocytes", Archives of Biochemistry and Biophysics, vol. 391, Issue 2, 2001, pp. 171-179.

Sharma et al., "RLIP76 (RALBP1)-mediated transport of leukotriene C4 (LTC4) in cancer cells: Implications in drug resistance", International Journal of Cancer, vol. 112, Issue 6, 2004, pp. 934-942.

Singhal et al., "Depletion of RLIP76 sensitizes lung cancer cells to doxorubicin", Biochemical Pharmacology, vol. 70, 2005, pp. 481-488.

Singhal et al., "Purification and functional reconstitution of intact ral-binding GTPase activating protein, RLIP76, in artificial liposomes", Acta Biochimica Polonica, vol. 48, No. 2, 2001, pp. 551-562.

Singhal et al., "RLIP76 in defense of radiation poisoning", International Journal of Radiation Oncology Biology Physics, vol. 72, No. 2, 2008, pp. 553-561.

Singhal et al., "Role of RLIP76 in lung cancer doxorubicin resistance: I. The ATPase activity of RLIP76 correlates with doxorubicin and 4-hydroxynonenal resistance in lung cancer cells", International Journal of Oncology, vol. 22, No. 2, 2003, pp. 365-375.

Singhal et al., "The role of PKCα and RLIP76 in transport-mediated doxorubicin-resistance in lung cancer", FEBS Letters, vol. 579, No. 30, 2005, pp. 4635-4641.

Soranzo et al., "Lack of Support for a Role of RLIP76 (RALBP1) in Response to Treatment or Predisposition to Epilepsy", Epilepsia, vol. 48, No. 4, 2007, pp. 674-683.

Stuckler et al., "RLIP76 Transports Vinorelbine and Mediates Drug Resistance in Non-Small Cell Lung Cancer", Cancer Research, vol. 65, No. 31, 2005, pp. 991-998.

Weiner, "An Overview of Monoclonal Antibody Therapy of Cancer", Seminars in Oncology, vol. 26, No. 4, Suppl. 12, 1999, pp. 41-50.

Wickramarachchi et al., "Identification of Membrane Anchoring Domains of RLIP76 Using Deletion Mutant Analysis", American Association of Cancer Research, 96th Annual Meeting Anaheim, CA, Apr. 16-20, 2005, (Abstract).

Yadav et al., "Identification of Membrane-Anchoring Domains of RLIP76 Using Deletion Mutant Analyses", Biochemistry, vol. 43, 2004, pp. 16243-16253.

Yadav et al., "POB1 over-expression inhibits RLIP76-mediated transport of glutathione-conjugates, drugs and promotes apoptosis", Biochemical and Biophysical Research Communications, vol. 328, 2005, pp. 1003-1009.

Yang et al., "Role of Glutathione S-Transferases in Protection against Lipid Peroxidation: Overexpression of hGSTA2-2 in K562 Cells Protects Against Hydrogen Peroxide-Induced Apoptosis and Inhibits JNK and Caspase 3 Activation", Journal of Biological Chemistry, vol. 276, No. 22, 2001, pp. 19220-19230.

Li et al., Chinese Pharmaceutical Journal, vol. 40, No. 19, 2005, pp. 1444-1448.

\* cited by examiner

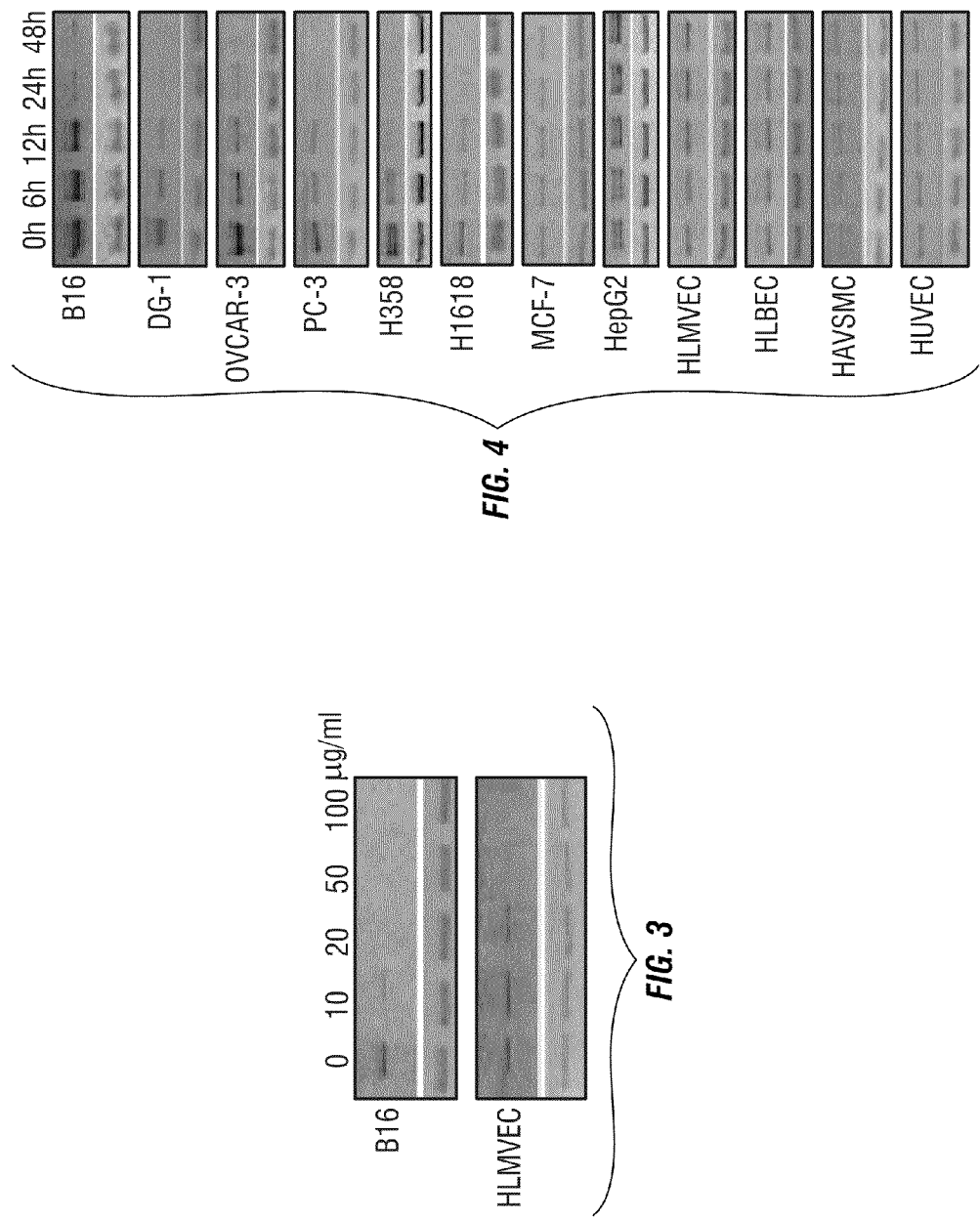

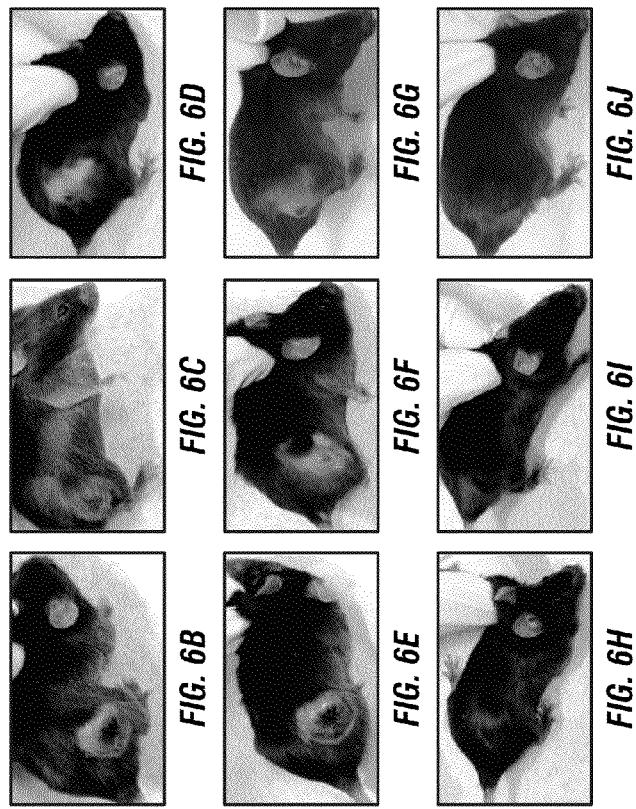
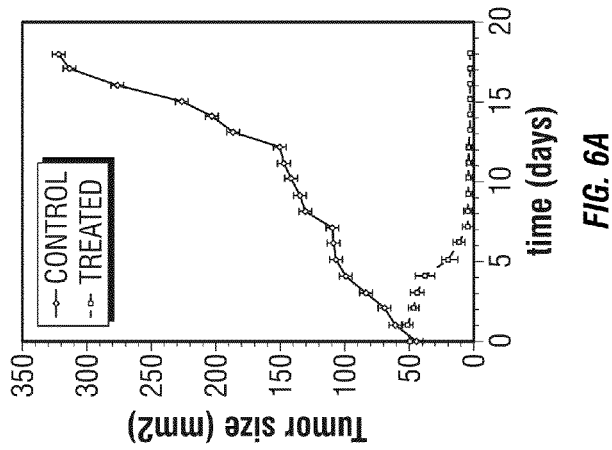
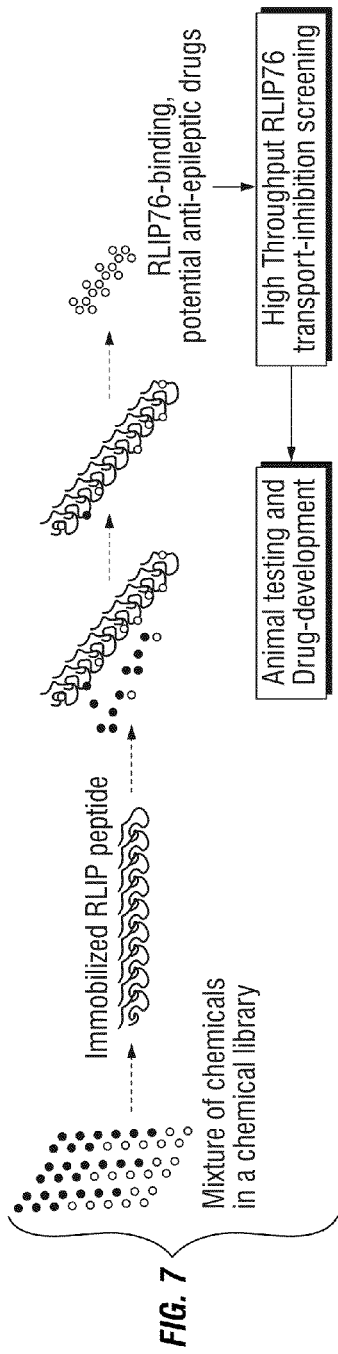

SEQUENCE LISTING

```
<160> NUMBER OF SEQ ID NOS: 24

<210> SEQ ID NO 1
<211> LENGTH: 4368
<212> TYPE: DNA
<213> ORGANISM: homo sapiens
<220> FEATURE:
<221> NAME/KEY: CDS
<222> LOCATION: (216)..(2183)

<400> SEQUENCE: 1
atcattgtaa acaggcagag gctgggcggg gtgggaatgg ggcgcccgag gccggcctgg      60
ggcgcagcgc aggaggcggc tccggtggct gcggcggcag cgtgagcgcg aggaggcgga     120
ggctgcggcg gggcggacgg tcgcgcggcg gcaggcacag gtgtaatgga taggtaacag     180
agaagacctc gtcccttcct agtcagggca tcagc atg act gag tgc ttc ctg        233
                                      Met Thr Glu Cys Phe Leu
                                      1               5 ccc ccc acc agc agc ccc agt gaa cac cgc agg gtg gag cat ggc agc       281
Pro Pro Thr Ser Ser Pro Ser Glu His Arg Arg Val Glu His Gly Ser
                10                  15                  20 ggg ctt acc cgg acc ccc agc tct gaa gag atc agc cct act aag ttt       329
Gly Leu Thr Arg Thr Pro Ser Ser Glu Glu Ile Ser Pro Thr Lys Phe
            25                  30                  35 cct gga ttg tac cgc act ggc gag ccc tca cct ccc cat gac atc ctc       377
Pro Gly Leu Tyr Arg Thr Gly Glu Pro Ser Pro Pro His Asp Ile Leu
        40                  45                  50 cat gag cct cct gat gta gtg tct gat gat gag aaa gat cat ggg aag       425
His Glu Pro Pro Asp Val Val Ser Asp Asp Glu Lys Asp His Gly Lys
55                  60                  65                  70 aaa aaa ggg aaa ttt aag aaa aag gaa aag agg act gaa ggc tat gca       473
Lys Lys Gly Lys Phe Lys Lys Lys Glu Lys Arg Thr Glu Gly Tyr Ala
                75                  80                  85 gcc ttt cag gaa gat agc tct gga gat gag gca gaa agt cct tct aaa       521
Ala Phe Gln Glu Asp Ser Ser Gly Asp Glu Ala Glu Ser Pro Ser Lys
            90                  95                  100 atg aag agg tcc aag gga atc cat gtt ttc aag aag ccc agc ttt tct       569
Met Lys Arg Ser Lys Gly Ile His Val Phe Lys Lys Pro Ser Phe Ser
        105                 110                 115 aaa aag aag gaa aag gat ttt aaa ata aaa gag aaa ccc aaa gaa gaa       617
Lys Lys Lys Glu Lys Asp Phe Lys Ile Lys Glu Lys Pro Lys Glu Glu
    120                 125                 130 aag cat aaa gaa gaa aag cac aaa gaa gaa aaa cat aaa gag aag aag       665
Lys His Lys Glu Glu Lys His Lys Glu Glu Lys His Lys Glu Lys Lys
135                 140                 145                 150 tca aaa gac ttg aca gca gct gat gtt gtt aaa cag tgg aag gaa aag       713
Ser Lys Asp Leu Thr Ala Ala Asp Val Val Lys Gln Trp Lys Glu Lys
```

-continued

```
                  155                 160                 165
aag aaa aag aaa aag cca att cag gag cca gag gtg cct cag att gat    761
Lys Lys Lys Lys Lys Pro Ile Gln Glu Pro Glu Val Pro Gln Ile Asp
            170                 175                 180 gtt cca aat ctc aaa ccc att ttt gga att cct ttg gct gat gca gta    809
Val Pro Asn Leu Lys Pro Ile Phe Gly Ile Pro Leu Ala Asp Ala Val
            185                 190                 195 gag agg acc atg atg tat gat ggc att cgg ctg cca gcc gtt ttc cgt    857
Glu Arg Thr Met Met Tyr Asp Gly Ile Arg Leu Pro Ala Val Phe Arg
    200                 205                 210 gaa tgt ata gat tac gta gag aag tat ggc atg aag tgt gaa ggc atc    905
Glu Cys Ile Asp Tyr Val Glu Lys Tyr Gly Met Lys Cys Glu Gly Ile
215                 220                 225                 230 tac aga gta tca gga att aaa tca aag gtg gat gag cta aaa gca gcc    953
Tyr Arg Val Ser Gly Ile Lys Ser Lys Val Asp Glu Leu Lys Ala Ala
                235                 240                 245 tat gac cgg gag gag tct aca aac ttg gaa gac tat gag cct aac act   1001
Tyr Asp Arg Glu Glu Ser Thr Asn Leu Glu Asp Tyr Glu Pro Asn Thr
            250                 255                 260 gta gcc agt ttg ctg aag cag tat ttg cga gac ctt cca gag aat ttg   1049
Val Ala Ser Leu Leu Lys Gln Tyr Leu Arg Asp Leu Pro Glu Asn Leu
            265                 270                 275 ctt acc aaa gag ctt atg ccc aga ttt gaa gag gct tgt ggg agg acc   1097
Leu Thr Lys Glu Leu Met Pro Arg Phe Glu Glu Ala Cys Gly Arg Thr
    280                 285                 290 acg gag act gag aaa gtg cag gaa ttc cag cgt tta ctc aaa gaa ctg   1145
Thr Glu Thr Glu Lys Val Gln Glu Phe Gln Arg Leu Leu Lys Glu Leu
295                 300                 305                 310 cca gaa tgt aac tat ctt ctg att tct tgg ctc att gtg cac atg gac   1193
Pro Glu Cys Asn Tyr Leu Leu Ile Ser Trp Leu Ile Val His Met Asp
                315                 320                 325 cat gtc att gca aag gaa ctg gaa aca aaa atg aat ata cag aac att   1241
His Val Ile Ala Lys Glu Leu Glu Thr Lys Met Asn Ile Gln Asn Ile
            330                 335                 340 tct ata gtg ctc agc cca act gtg cag atc agc aat cga gtc ctg tat   1289
Ser Ile Val Leu Ser Pro Thr Val Gln Ile Ser Asn Arg Val Leu Tyr
            345                 350                 355 gtg ttt ttc aca cat gtg caa gaa ctc ttt gga aat gtg gta cta aag   1337
Val Phe Phe Thr His Val Gln Glu Leu Phe Gly Asn Val Val Leu Lys
    360                 365                 370 caa gtg atg aaa cct ctg cga tgg tct aac atg gcc acg atg ccc acg   1385
Gln Val Met Lys Pro Leu Arg Trp Ser Asn Met Ala Thr Met Pro Thr
375                 380                 385                 390 ctg cca gag acc cag gcg ggc atc aag gag gag atc agg aga cag gag   1433
Leu Pro Glu Thr Gln Ala Gly Ile Lys Glu Glu Ile Arg Arg Gln Glu
                395                 400                 405 ttt ctt ttg aat tgt tta cat cga gat ctg cag ggt ggg ata aag gat   1481
Phe Leu Leu Asn Cys Leu His Arg Asp Leu Gln Gly Gly Ile Lys Asp
            410                 415                 420 ttg tct aaa gaa gaa aga tta tgg gaa gta caa aga att ttg aca gcc   1529
Leu Ser Lys Glu Glu Arg Leu Trp Glu Val Gln Arg Ile Leu Thr Ala
            425                 430                 435 ctc aaa aga aaa ctg aga gaa gct aaa aga cag gag tgt gaa acc aag   1577
Leu Lys Arg Lys Leu Arg Glu Ala Lys Arg Gln Glu Cys Glu Thr Lys
    440                 445                 450 att gca caa gag ata gcc agt ctt tca aaa gag gat gtt tcc aaa gaa   1625
Ile Ala Gln Glu Ile Ala Ser Leu Ser Lys Glu Asp Val Ser Lys Glu
455                 460                 465                 470 gag atg aat gaa aat gaa gaa gtt ata aat att ctc ctt gct cag gag   1673
Glu Met Asn Glu Asn Glu Glu Val Ile Asn Ile Leu Leu Ala Gln Glu
```

```
                         475                 480                 485
aat gag atc ctg act gaa cag gag gag ctc ctg gcc atg gag cag ttt      1721
Asn Glu Ile Leu Thr Glu Gln Glu Glu Leu Leu Ala Met Glu Gln Phe
                490                 495                 500 ctg cgc cgg cag att gcc tca gaa aaa gaa gag att gaa cgc ctc aga      1769
Leu Arg Arg Gln Ile Ala Ser Glu Lys Glu Glu Ile Glu Arg Leu Arg
            505                 510                 515 gct gag att gct gaa att cag agt cgc cag cag cac ggc cga agt gag      1817
Ala Glu Ile Ala Glu Ile Gln Ser Arg Gln Gln His Gly Arg Ser Glu
        520                 525                 530 act gag gag tac tcc tcc gag agc gag agc gag agt gag gat gag gag      1865
Thr Glu Glu Tyr Ser Ser Glu Ser Glu Ser Glu Ser Glu Asp Glu Glu
535                 540                 545                 550 gag ctg cag atc att ctg gaa gac tta cag aga cag aac gaa gag ctg      1913
Glu Leu Gln Ile Ile Leu Glu Asp Leu Gln Arg Gln Asn Glu Glu Leu
                555                 560                 565 gaa ata aag aac aat cat ttg aat caa gca att cat gag gag cgc gag      1961
Glu Ile Lys Asn Asn His Leu Asn Gln Ala Ile His Glu Glu Arg Glu
            570                 575                 580 gcc atc atc gag ctg cgc gtg cag ctg cgg ctg ctc cag atg cag cga      2009
Ala Ile Ile Glu Leu Arg Val Gln Leu Arg Leu Leu Gln Met Gln Arg
        585                 590                 595 gcc aag gcc gag cag cag gcg cag gag gac gag gag cct gag tgg cgc      2057
Ala Lys Ala Glu Gln Gln Ala Gln Glu Asp Glu Glu Pro Glu Trp Arg
600                 605                 610 ggg ggt gcc gtc cag ccg ccc aga gac ggc gtc ctt gag cca aaa gca      2105
Gly Gly Ala Val Gln Pro Pro Arg Asp Gly Val Leu Glu Pro Lys Ala
615                 620                 625                 630 gct aaa gag cag cca aag gca ggc aag gag ccg gca aag cca tcg ccc      2153
Ala Lys Glu Gln Pro Lys Ala Gly Lys Glu Pro Ala Lys Pro Ser Pro
                635                 640                 645 agc agg gat agg aag gag acg tcc atc tga gcagcctgcg tggccgtctg        2203
Ser Arg Asp Arg Lys Glu Thr Ser Ile
            650                 655 gagtccgtga gactgaaagg acccgtgcat cttactgtaa cccgggggcc aggccggctc    2263
tctcgctgta cattctgtaa aggtgtcttc tcttctcaga ctcttcctct gtcacacgtc    2323
tgactccttc acgtcaggct caggttccat gggaggacga agcagtggac gcattgtggg    2383
ctttagggac agatgagttt tccagatagt gtcagcttat ttgaagatta attttctttg    2443
ttaacttaaa ataactattt taaccctgta gtggcttctt tttaaaccaa aaaccgtctt    2503
tctttgcttt tttatcacag cagaatcagg atctcttttct cattcaaggg gggaaccacc   2563
ccaggtcagc gctgcgcctg ctgtggccgc cgcgagccac gccctctggg atctctggta    2623
ccgtcactct tgcttgtgcc ttccacacct tctcggtgca gatccctatg ggggagctgc    2683
ctcacgttct ctgactggtc agagcagcgc ctggtgggtg ttccctggcc cactctcctc    2743
tctccttctg cagttctaaa ccacagtcta taagcccgag tcaccaggac ggcctgtctg    2803
gccacagaca ggggctgcct gtggagcctg cccaccggcc cccggcagtg cagtccagcg    2863
gggaggaggc tgcccgttcc tgccagttcc tcactgcggg gaccagcaaa ggccttctca    2923 ctggggttggt caaaggtagt caccttggcc tggtgcatcc acagaggatg ttgttcaaac   2983
cagaaatctt ttaaacgact gaccttcctt aaaaacagaa tgactccgat tgcttgcttg    3043
ggctagaatg tacacgtctc cttgcctgaa taagccatat atatgctctt aaacaaaagt    3103
ttgaaattat ccatatcatc tcagtgaacc tactggtgga ctcccaattg acaagattga    3163
gcaatagaaa aaaattcctt tcctttgaat gatagctgtg attcaccccca ccccattttc    3223
```

```
ttgtttctgg tccatccgat gagacggatg ctctgatgct ctgaggcttc tgggaggctg    3283
ggccctggag gcaacgtgct gcaggcgcac tctgtcagag tgaacagcac cgcgagacag    3343
gccaggctcg tggctcggaa gacaaacccc acacacactc aagggtcga aaacaaaccc     3403 cacacgaggg ctctcacctc cttctcctag gtagtattta ttttcagcac ctgtttgatg    3463 cagttttaa tcctctacct attgcactgt tgtgactcgt tggccattat ttgattttg      3523 tacgaaaaaa agctttgtta tagaaatcag catactattt ttttaaatct ggagagaaga    3583
tattctggtg actgaaagta tggtcgggtg tcagatataa atgtgcaaat gccttcttgc    3643
tgtcctgtcg gtctcagtac gttcacttta tagctgctgg caatatcgaa ggttcctttt    3703
ttgtttgtgt aaactctaat ttctatcaag gtgtcatgga tttttaaaat tagtatttca    3763
ttacaaatgt ctcagcattg gttaactaat ttttgccagg accattattg atcaagcaaa    3823
taaattcaac agccatttgg gaaaagaaa agcttctagt ttttttgtac acattctttc     3883
tgtgaggaga ttgagtactc tgcagctggc gaggagttgg ttgaggcact tcttcaaggc    3943 caaggggaa acagtgttt tgtttccagc tcactttgta cccctcacct ctgcagacac       4003
ggggagaacc ccggacccct ggcatgcatg ctggcggcgg catgcctccc ttccacaagc    4063
ccatgctgct gcagagggag cctgtgtttg caaaacccag tggactgggc tgggtctgct    4123
gtctgagcag ctcctggctc cggtgggaac tgcacacaag tccactgcc tggcttggcc     4183 ccaggcattg caattgacag acatttgcat ttcatacggt aaatgaggac tcagcacagc    4243
caaccataat cagcatgtct gggatagact ggtctagaat aaaaatgaag tttccattgc    4303
tttgtttgct ttaaaaattc cacaattaaa atatctgtca ttgaaagctt aaaaaaaaaa    4363
aaaaa                                                                 4368
```

<210> SEQ ID NO 2
<211> LENGTH: 655
<212> TYPE: PRT
<213> ORGANISM: homo sapiens

<400> SEQUENCE: 2

```
Met Thr Glu Cys Phe Leu Pro Pro Thr Ser Ser Pro Ser Glu His Arg
1               5                   10                  15

Arg Val Glu His Gly Ser Gly Leu Thr Arg Thr Pro Ser Ser Glu Glu
            20                  25                  30

Ile Ser Pro Thr Lys Phe Pro Gly Leu Tyr Arg Thr Gly Glu Pro Ser
        35                  40                  45

Pro Pro His Asp Ile Leu His Glu Pro Pro Asp Val Val Ser Asp Asp
    50                  55                  60

Glu Lys Asp His Gly Lys Lys Gly Lys Phe Lys Lys Glu Lys
65                  70                  75                  80

Arg Thr Glu Gly Tyr Ala Ala Phe Gln Glu Asp Ser Ser Gly Asp Glu
                85                  90                  95

Ala Glu Ser Pro Ser Lys Met Lys Arg Ser Lys Gly Ile His Val Phe
            100                 105                 110

Lys Lys Pro Ser Phe Ser Lys Lys Lys Glu Lys Asp Phe Lys Ile Lys
        115                 120                 125

Glu Lys Pro Lys Glu Glu Lys His Lys Glu Glu Lys His Lys Glu Glu
    130                 135                 140

Lys His Lys Glu Lys Lys Ser Lys Asp Leu Thr Ala Ala Asp Val Val
145                 150                 155                 160

Lys Gln Trp Lys Glu Lys Lys Lys Lys Lys Pro Ile Gln Glu Pro
                165                 170                 175
```

-continued

```
Glu Val Pro Gln Ile Asp Val Pro Asn Leu Lys Pro Ile Phe Gly Ile
            180                 185                 190
Pro Leu Ala Asp Ala Val Glu Arg Thr Met Met Tyr Asp Gly Ile Arg
            195                 200                 205
Leu Pro Ala Val Phe Arg Glu Cys Ile Asp Tyr Val Glu Lys Tyr Gly
    210                 215                 220
Met Lys Cys Glu Gly Ile Tyr Arg Val Ser Gly Ile Lys Ser Lys Val
225                 230                 235                 240
Asp Glu Leu Lys Ala Ala Tyr Asp Arg Glu Glu Ser Thr Asn Leu Glu
                245                 250                 255
Asp Tyr Glu Pro Asn Thr Val Ala Ser Leu Leu Lys Gln Tyr Leu Arg
                260                 265                 270
Asp Leu Pro Glu Asn Leu Leu Thr Lys Glu Leu Met Pro Arg Phe Glu
            275                 280                 285
Glu Ala Cys Gly Arg Thr Thr Glu Thr Glu Lys Val Gln Glu Phe Gln
            290                 295                 300
Arg Leu Leu Lys Glu Leu Pro Glu Cys Asn Tyr Leu Leu Ile Ser Trp
305                 310                 315                 320
Leu Ile Val His Met Asp His Val Ile Ala Lys Glu Leu Glu Thr Lys
                325                 330                 335
Met Asn Ile Gln Asn Ile Ser Ile Val Leu Ser Pro Thr Val Gln Ile
            340                 345                 350
Ser Asn Arg Val Leu Tyr Val Phe Phe Thr His Val Gln Glu Leu Phe
            355                 360                 365
Gly Asn Val Val Leu Lys Gln Val Met Lys Pro Leu Arg Trp Ser Asn
        370                 375                 380
Met Ala Thr Met Pro Thr Leu Pro Glu Thr Gln Ala Gly Ile Lys Glu
385                 390                 395                 400
Glu Ile Arg Arg Gln Glu Phe Leu Leu Asn Cys Leu His Arg Asp Leu
                405                 410                 415
Gln Gly Gly Ile Lys Asp Leu Ser Lys Glu Glu Arg Leu Trp Glu Val
            420                 425                 430
Gln Arg Ile Leu Thr Ala Leu Lys Arg Lys Leu Arg Glu Ala Lys Arg
        435                 440                 445
Gln Glu Cys Glu Thr Lys Ile Ala Gln Glu Ile Ala Ser Leu Ser Lys
    450                 455                 460
Glu Asp Val Ser Lys Glu Met Asn Glu Asn Glu Glu Val Ile Asn
465                 470                 475                 480
Ile Leu Leu Ala Gln Glu Asn Glu Ile Leu Thr Glu Gln Glu Glu Leu
                485                 490                 495
Leu Ala Met Glu Gln Phe Leu Arg Arg Gln Ile Ala Ser Glu Lys Glu
            500                 505                 510
Glu Ile Glu Arg Leu Arg Ala Glu Ile Ala Glu Ile Gln Ser Arg Gln
            515                 520                 525
Gln His Gly Arg Ser Glu Thr Glu Tyr Ser Ser Glu Ser Glu Ser
    530                 535                 540
Glu Ser Glu Asp Glu Glu Leu Gln Ile Ile Leu Glu Asp Leu Gln
545                 550                 555                 560
Arg Gln Asn Glu Glu Leu Glu Ile Lys Asn Asn His Leu Asn Gln Ala
                565                 570                 575
Ile His Glu Glu Arg Glu Ala Ile Ile Glu Leu Arg Val Gln Leu Arg
            580                 585                 590
Leu Leu Gln Met Gln Arg Ala Lys Ala Glu Gln Gln Ala Gln Glu Asp
```

```
                    595                 600                 605
Glu Glu Pro Glu Trp Arg Gly Gly Ala Val Gln Pro Pro Arg Asp Gly
            610                 615                 620

Val Leu Glu Pro Lys Ala Ala Lys Glu Gln Pro Lys Ala Gly Lys Glu
625                 630                 635                 640

Pro Ala Lys Pro Ser Pro Ser Arg Asp Arg Lys Glu Thr Ser Ile
                645                 650                 655

<210> SEQ ID NO 3
<211> LENGTH: 66
<212> TYPE: PRT
<213> ORGANISM: artificial sequence
<220> FEATURE:
<223> OTHER INFORMATION: epitope region comprising residues 154-219

<400> SEQUENCE: 3

Leu Thr Ala Ala Asp Val Val Lys Gln Trp Lys Glu Lys Lys Lys Lys
1               5                   10                  15

Lys Lys Pro Ile Gln Glu Pro Glu Val Pro Gln Ile Asp Val Pro Asn
                20                  25                  30

Leu Lys Pro Ile Phe Gly Ile Pro Leu Ala Asp Ala Val Glu Arg Thr
            35                  40                  45

Met Met Tyr Asp Gly Ile Arg Leu Pro Ala Val Phe Arg Glu Cys Ile
        50                  55                  60

Asp Tyr
65

<210> SEQ ID NO 4
<211> LENGTH: 15
<212> TYPE: PRT
<213> ORGANISM: artificial sequence
<220> FEATURE:
<223> OTHER INFORMATION: epitope region comprising residues 171-185

<400> SEQUENCE: 4

Lys Pro Ile Gln Glu Pro Glu Val Pro Gln Ile Asp Val Pro Asn
1               5                   10                  15

<210> SEQ ID NO 5
<211> LENGTH: 26
<212> TYPE: DNA
<213> ORGANISM: artificial sequence
<220> FEATURE:
<223> OTHER INFORMATION: upstream primer sequence for clone of full
      length RLIP

<400> SEQUENCE: 5
ggcggatcca tgactgagtg cttcct                                        26

<210> SEQ ID NO 6
<211> LENGTH: 34
<212> TYPE: DNA
<213> ORGANISM: artificial sequence
<220> FEATURE:
<223> OTHER INFORMATION: downstream primer sequence for clone of full
      length RLIP

<400> SEQUENCE: 6
ccgctcgagt agatggacgt ctccttccta tccc                               34

<210> SEQ ID NO 7
<211> LENGTH: 30
<212> TYPE: DNA
<213> ORGANISM: artificial sequence
```

<220> FEATURE:
<223> OTHER INFORMATION: mutagenic upstream primer for deletion mutant 203-219

<400> SEQUENCE: 7
gtagagagga ccatggtaga gaagtatggc       30

<210> SEQ ID NO 8
<211> LENGTH: 31
<212> TYPE: DNA
<213> ORGANISM: artificial sequence
<220> FEATURE:
<223> OTHER INFORMATION: mutagenic upstream primer for deletion mutant 154-171

<400> SEQUENCE: 8
gaagaagtca aaagacaagc caattcagga g       31

<210> SEQ ID NO 9
<211> LENGTH: 28
<212> TYPE: DNA
<213> ORGANISM: artificial sequence
<220> FEATURE:
<223> OTHER INFORMATION: mutagenic upstream primer for deletion mutant 171-185

<400> SEQUENCE: 9
gaagaaaaag aaactcaaac ccattttt       28

<210> SEQ ID NO 10
<211> LENGTH: 31
<212> TYPE: DNA
<213> ORGANISM: artificial sequence
<220> FEATURE:
<223> OTHER INFORMATION: mutagenic upstream prime for deletion mutant 154-219

<400> SEQUENCE: 10
gaagaagtca aaagacgtag agaagtatgg c       31

<210> SEQ ID NO 11
<211> LENGTH: 31
<212> TYPE: DNA
<213> ORGANISM: artificial sequence
<220> FEATURE:
<223> OTHER INFORMATION: mutagenic upstream primer for deletion mutant 415-448

<400> SEQUENCE: 11
gaattgttta catcgacagg agtgtgaaac c       31

<210> SEQ ID NO 12
<211> LENGTH: 28
<212> TYPE: DNA
<213> ORGANISM: artificial sequence
<220> FEATURE:
<223> OTHER INFORMATION: mutagenic upstream primer for deletion mutant 65-80

<400> SEQUENCE: 12
gtgtctgatg ataggactga aggctatg       28

<210> SEQ ID NO 13
<211> LENGTH: 23
<212> TYPE: DNA
<213> ORGANISM: artificial sequence
<220> FEATURE:
<223> OTHER INFORMATION: targeted cDNA corresponding to nucleotides 508-528 of ral A binding protein 1

<400> SEQUENCE: 13
aagaaaaagc caattcagga gcc                                          23

<210> SEQ ID NO 14
<211> LENGTH: 23
<212> TYPE: RNA
<213> ORGANISM: artificial sequence
<220> FEATURE:
<223> OTHER INFORMATION: corresponding sense siRNA strand for targeted
      cDNA
<220> FEATURE:
<221> NAME/KEY: d
<222> LOCATION: (22)..(23)
<223> OTHER INFORMATION: dT

<400> SEQUENCE: 14
gaaaaagcca auucaggagc cdd                                          23

<210> SEQ ID NO 15
<211> LENGTH: 23
<212> TYPE: RNA
<213> ORGANISM: artificial sequence
<220> FEATURE:
<223> OTHER INFORMATION: corresponding antisense siRNA strand for
      targeted cDNA
<220> FEATURE:
<221> NAME/KEY: d
<222> LOCATION: (22)..(23)
<223> OTHER INFORMATION: dT

<400> SEQUENCE: 15
ggcuccugaa uuggcuuuuu cdd                                          23

<210> SEQ ID NO 16
<211> LENGTH: 23
<212> TYPE: RNA
<213> ORGANISM: Artificial Sequence
<220> FEATURE:
<223> OTHER INFORMATION: scrambled sense siRNA strand
<220> FEATURE:
<221> NAME/KEY: d
<222> LOCATION: (22)..(23)
<223> OTHER INFORMATION: dT

<400> SEQUENCE: 16
guaacugcaa cgauuucgau gdd                                          23

<210> SEQ ID NO 17
<211> LENGTH: 23
<212> TYPE: RNA
<213> ORGANISM: artificial sequence
<220> FEATURE:
<223> OTHER INFORMATION: scrambled antisense siRNA strand
<220> FEATURE:
<221> NAME/KEY: d
<222> LOCATION: (22)..(23)
<223> OTHER INFORMATION: dT

<400> SEQUENCE: 17
caucgaaauc guugcaguua cdd                                          23

<210> SEQ ID NO 18
<211> LENGTH: 21
<212> TYPE: DNA
<213> ORGANISM: artificial sequence
<220> FEATURE:
<223> OTHER INFORMATION: phosphorothioate antisense oligonucleotides -continued

```
<400> SEQUENCE: 18
ggctcctgaa ttggcttttt c                                              21

<210> SEQ ID NO 19
<211> LENGTH: 22
<212> TYPE: DNA
<213> ORGANISM: artificial sequence
<220> FEATURE:
<223> OTHER INFORMATION: corresponding silencing RNA sequence to the
      phosphorothioate antisense oligonucleotide

<400> SEQUENCE: 19
aagaaaagcc aattcaggag cc                                             22

<210> SEQ ID NO 20
<211> LENGTH: 198
<212> TYPE: DNA
<213> ORGANISM: artificial sequence
<220> FEATURE:
<223> OTHER INFORMATION: epitope nucleotide sequence corresponding to
      residues 154-219

<400> SEQUENCE: 20
ttgacagcag ctgatgttgt taaacagtgg aaggaaaaga agaaaaagaa aaagccaatt    60
caggagccag aggtgcctca gattgatgtt ccaaatctca aacccatttt tggaattcct   120
ttggctgatg cagtagagag gaccatgatg tatgatggca ttcggctgcc agccgttttc   180
cgtgaatgta tagattac                                                 198

<210> SEQ ID NO 21
<211> LENGTH: 45
<212> TYPE: DNA
<213> ORGANISM: artificial sequence
<220> FEATURE:
<223> OTHER INFORMATION: epitope nucleotide sequence corresponding to
      residues 171-185

<400> SEQUENCE: 21
aagccaattc aggagccaga ggtgcctcag attgatgttc caaat                    45

<210> SEQ ID NO 22
<211> LENGTH: 1968
<212> TYPE: DNA
<213> ORGANISM: homo sapiens
<220> FEATURE:
<221> NAME/KEY: CDS
<222> LOCATION: (1)..(1965)

<400> SEQUENCE: 22 atg act gag tgc ttc ctg ccc ccc acc agc agc ccc agt gaa cac cgc     48
Met Thr Glu Cys Phe Leu Pro Pro Thr Ser Ser Pro Ser Glu His Arg
1               5                   10                  15 agg gtg gag cat ggc agc ggg ctt acc cgg acc ccc agc tct gaa gag     96
Arg Val Glu His Gly Ser Gly Leu Thr Arg Thr Pro Ser Ser Glu Glu
                20                  25                  30 atc agc cct act aag ttt cct gga ttg tac cgc act ggc gag ccc tca    144
Ile Ser Pro Thr Lys Phe Pro Gly Leu Tyr Arg Thr Gly Glu Pro Ser
            35                  40                  45 cct ccc cat gac atc ctc cat gag cct cct gat gta gtg tct gat gat    192
Pro Pro His Asp Ile Leu His Glu Pro Pro Asp Val Val Ser Asp Asp
        50                  55                  60 gag aaa gat cat ggg aag aaa aaa ggg aaa ttt aag aaa aag gaa aag    240
Glu Lys Asp His Gly Lys Lys Lys Gly Lys Phe Lys Lys Lys Glu Lys
65                  70                  75                  80
```

```
agg act gaa ggc tat gca gcc ttt cag gaa gat agc tct gga gat gag    288
Arg Thr Glu Gly Tyr Ala Ala Phe Gln Glu Asp Ser Ser Gly Asp Glu
             85                  90                  95 gca gaa agt cct tct aaa atg aag agg tcc aag gga atc cat gtt ttc    336
Ala Glu Ser Pro Ser Lys Met Lys Arg Ser Lys Gly Ile His Val Phe
            100                 105                 110 aag aag ccc agc ttt tct aaa aag aag gaa aag gat ttt aaa ata aaa    384
Lys Lys Pro Ser Phe Ser Lys Lys Lys Glu Lys Asp Phe Lys Ile Lys
            115                 120                 125 gag aaa ccc aaa gaa gaa aag cat aaa gaa gaa aag cac aaa gaa gaa    432
Glu Lys Pro Lys Glu Glu Lys His Lys Glu Glu Lys His Lys Glu Glu
        130                 135                 140 aaa cat aaa gag aag aag tca aaa gac ttg aca gca gct gat gtt gtt    480
Lys His Lys Glu Lys Lys Ser Lys Asp Leu Thr Ala Ala Asp Val Val
145                 150                 155                 160 aaa cag tgg aag gaa aag aag aaa aag aaa aag cca att cag gag cca    528
Lys Gln Trp Lys Glu Lys Lys Lys Lys Lys Pro Ile Gln Glu Pro
                165                 170                 175 gag gtg cct cag att gat gtt cca aat ctc aaa ccc att ttt gga att    576
Glu Val Pro Gln Ile Asp Val Pro Asn Leu Lys Pro Ile Phe Gly Ile
            180                 185                 190 cct ttg gct gat gca gta gag agg acc atg atg tat gat ggc att cgg    624
Pro Leu Ala Asp Ala Val Glu Arg Thr Met Met Tyr Asp Gly Ile Arg
            195                 200                 205 ctg cca gcc gtt ttc cgt gaa tgt ata gat tac gta gag aag tat ggc    672
Leu Pro Ala Val Phe Arg Glu Cys Ile Asp Tyr Val Glu Lys Tyr Gly
            210                 215                 220 atg aag tgt gaa ggc atc tac aga gta tca gga att aaa tca aag gtg    720
Met Lys Cys Glu Gly Ile Tyr Arg Val Ser Gly Ile Lys Ser Lys Val
225                 230                 235                 240 gat gag cta aaa gca gcc tat gac cgg gag gag tct aca aac ttg gaa    768
Asp Glu Leu Lys Ala Ala Tyr Asp Arg Glu Glu Ser Thr Asn Leu Glu
                245                 250                 255 gac tat gag cct aac act gta gcc agt ttg ctg aag cag tat ttg cga    816
Asp Tyr Glu Pro Asn Thr Val Ala Ser Leu Leu Lys Gln Tyr Leu Arg
            260                 265                 270 gac ctt cca gag aat ttg ctt acc aaa gag ctt atg ccc aga ttt gaa    864
Asp Leu Pro Glu Asn Leu Leu Thr Lys Glu Leu Met Pro Arg Phe Glu
            275                 280                 285 gag gct tgt ggg agg acc acg gag act gag aaa gtg cag gaa ttc cag    912
Glu Ala Cys Gly Arg Thr Thr Glu Thr Glu Lys Val Gln Glu Phe Gln
            290                 295                 300 cgt tta ctc aaa gaa ctg cca gaa tgt aac tat ctt ctg att tct tgg    960
Arg Leu Leu Lys Glu Leu Pro Glu Cys Asn Tyr Leu Leu Ile Ser Trp
305                 310                 315                 320 ctc att gtg cac atg gac cat gtc att gca aag gaa ctg gaa aca aaa   1008
Leu Ile Val His Met Asp His Val Ile Ala Lys Glu Leu Glu Thr Lys
                325                 330                 335 atg aat ata cag aac att tct ata gtc ctc agc cca act gtg cag atc   1056
Met Asn Ile Gln Asn Ile Ser Ile Val Leu Ser Pro Thr Val Gln Ile
            340                 345                 350 agc aat cga gtc ctg tat gtg ttt ttc aca cat gtg caa gaa ctc ttt   1104
Ser Asn Arg Val Leu Tyr Val Phe Phe Thr His Val Gln Glu Leu Phe
            355                 360                 365 gga aat gtg gta cta aag caa gtg atg aaa cct ctg cga tgg tct aac   1152
Gly Asn Val Val Leu Lys Gln Val Met Lys Pro Leu Arg Trp Ser Asn
        370                 375                 380 atg gcc acg atg ccc acg ctg cca gag acc cag gcg ggc atc aag gag   1200
Met Ala Thr Met Pro Thr Leu Pro Glu Thr Gln Ala Gly Ile Lys Glu
385                 390                 395                 400
```

```
gag atc agg aga cag gag ttt ctt ttg aat tgt tta cat cga gat ctg      1248
Glu Ile Arg Arg Gln Glu Phe Leu Leu Asn Cys Leu His Arg Asp Leu
            405                 410                 415 cag ggt ggg ata aag gat ttg tct aaa gaa gaa aga tta tgg gaa gta      1296
Gln Gly Gly Ile Lys Asp Leu Ser Lys Glu Glu Arg Leu Trp Glu Val
        420                 425                 430 caa aga att ttg aca gcc ctc aaa aga aaa ctg aga gaa gct aaa aga      1344
Gln Arg Ile Leu Thr Ala Leu Lys Arg Lys Leu Arg Glu Ala Lys Arg
    435                 440                 445 cag gag tgt gaa acc aag att gca caa gag ata gcc agt ctt tca aaa      1392
Gln Glu Cys Glu Thr Lys Ile Ala Gln Glu Ile Ala Ser Leu Ser Lys
450                 455                 460 gag gat gtt tcc aaa gaa gag atg aat gaa aat gaa gaa gtt ata aat      1440
Glu Asp Val Ser Lys Glu Glu Met Asn Glu Asn Glu Glu Val Ile Asn
465                 470                 475                 480 att ctc ctt gct cag gag aat gag atc ctg act gaa cag gag gag ctc      1488
Ile Leu Leu Ala Gln Glu Asn Glu Ile Leu Thr Glu Gln Glu Glu Leu
                485                 490                 495 ctg gcc atg gag cag ttt ctg cgc cgg cag att gcc tca gaa aaa gaa      1536
Leu Ala Met Glu Gln Phe Leu Arg Arg Gln Ile Ala Ser Glu Lys Glu
            500                 505                 510 gag att gaa cgc ctc aga gct gag att gct gaa att cag agt cgc cag      1584
Glu Ile Glu Arg Leu Arg Ala Glu Ile Ala Glu Ile Gln Ser Arg Gln
        515                 520                 525 cag cac ggc cga agt gag act gag gag tac tcc tcc gag agc gag agc      1632
Gln His Gly Arg Ser Glu Thr Glu Glu Tyr Ser Ser Glu Ser Glu Ser
    530                 535                 540 gag agt gag gat gag gag gag ctg cag atc att ctg gaa gac tta cag      1680
Glu Ser Glu Asp Glu Glu Glu Leu Gln Ile Ile Leu Glu Asp Leu Gln
545                 550                 555                 560 aga cag aac gaa gag ctg gaa ata aag aac aat cat ttg aat caa gca      1728
Arg Gln Asn Glu Glu Leu Glu Ile Lys Asn Asn His Leu Asn Gln Ala
                565                 570                 575 att cat gag gag cgc gag gcc atc atc gag ctg cgc gtg cag ctg cgg      1776
Ile His Glu Glu Arg Glu Ala Ile Ile Glu Leu Arg Val Gln Leu Arg
            580                 585                 590 ctg ctc cag atg cag cga gcc aag gcc gag cag cag gcg cag gag gac      1824
Leu Leu Gln Met Gln Arg Ala Lys Ala Glu Gln Gln Ala Gln Glu Asp
        595                 600                 605 gag gag cct gag tgg cgc ggg ggt gcc gtc cag ccg ccc aga gac ggc      1872
Glu Glu Pro Glu Trp Arg Gly Gly Ala Val Gln Pro Pro Arg Asp Gly
    610                 615                 620 gtc ctt gag cca aaa gca gct aaa gag cag cca aag gca ggc aag gag      1920
Val Leu Glu Pro Lys Ala Ala Lys Glu Gln Pro Lys Ala Gly Lys Glu
625                 630                 635                 640 ccg gca aag cca tcg ccc agc agg gat agg aag gag acg tcc atc tga      1968
Pro Ala Lys Pro Ser Pro Ser Arg Asp Arg Lys Glu Thr Ser Ile
                645                 650                 655

<210> SEQ ID NO 23
<211> LENGTH: 655
<212> TYPE: PRT
<213> ORGANISM: homo sapiens

<400> SEQUENCE: 23

Met Thr Glu Cys Phe Leu Pro Pro Thr Ser Pro Ser Glu His Arg
1               5                   10                  15

Arg Val Glu His Gly Ser Gly Leu Thr Arg Thr Pro Ser Glu Glu
            20                  25                  30

Ile Ser Pro Thr Lys Phe Pro Gly Leu Tyr Arg Thr Gly Glu Pro Ser
        35                  40                  45
```

-continued

Pro Pro His Asp Ile Leu His Glu Pro Pro Asp Val Val Ser Asp Asp
         50                  55                  60

Glu Lys Asp His Gly Lys Lys Gly Lys Phe Lys Lys Glu Lys
65              70                  75                  80

Arg Thr Glu Gly Tyr Ala Ala Phe Gln Glu Asp Ser Ser Gly Asp Glu
                 85                  90                  95

Ala Glu Ser Pro Ser Lys Met Lys Arg Ser Lys Gly Ile His Val Phe
             100                 105                 110

Lys Lys Pro Ser Phe Ser Lys Lys Lys Glu Lys Asp Phe Lys Ile Lys
         115                 120                 125

Glu Lys Pro Lys Glu Glu Lys His Lys Glu Glu Lys His Lys Glu Glu
         130                 135                 140

Lys His Lys Glu Lys Lys Ser Lys Asp Leu Thr Ala Ala Asp Val Val
145                 150                 155                 160

Lys Gln Trp Lys Glu Lys Lys Lys Lys Lys Pro Ile Gln Glu Pro
                 165                 170                 175

Glu Val Pro Gln Ile Asp Val Pro Asn Leu Lys Pro Ile Phe Gly Ile
                 180                 185                 190

Pro Leu Ala Asp Ala Val Glu Arg Thr Met Met Tyr Asp Gly Ile Arg
             195                 200                 205

Leu Pro Ala Val Phe Arg Glu Cys Ile Asp Tyr Val Glu Lys Tyr Gly
210                 215                 220

Met Lys Cys Glu Gly Ile Tyr Arg Val Ser Gly Ile Lys Ser Lys Val
225                 230                 235                 240

Asp Glu Leu Lys Ala Ala Tyr Asp Arg Glu Glu Ser Thr Asn Leu Glu
             245                 250                 255

Asp Tyr Glu Pro Asn Thr Val Ala Ser Leu Leu Lys Gln Tyr Leu Arg
             260                 265                 270

Asp Leu Pro Glu Asn Leu Leu Thr Lys Glu Leu Met Pro Arg Phe Glu
         275                 280                 285

Glu Ala Cys Gly Arg Thr Thr Glu Thr Glu Lys Val Gln Glu Phe Gln
290                 295                 300

Arg Leu Leu Lys Glu Leu Pro Glu Cys Asn Tyr Leu Leu Ile Ser Trp
305                 310                 315                 320

Leu Ile Val His Met Asp His Val Ile Ala Lys Glu Leu Glu Thr Lys
                 325                 330                 335

Met Asn Ile Gln Asn Ile Ser Ile Val Leu Ser Pro Thr Val Gln Ile
             340                 345                 350

Ser Asn Arg Val Leu Tyr Val Phe Phe Thr His Val Gln Glu Leu Phe
         355                 360                 365

Gly Asn Val Val Leu Lys Gln Val Met Lys Pro Leu Arg Trp Ser Asn
370                 375                 380

Met Ala Thr Met Pro Thr Leu Pro Glu Thr Gln Ala Gly Ile Lys Glu
385                 390                 395                 400

Glu Ile Arg Arg Gln Glu Phe Leu Leu Asn Cys Leu His Arg Asp Leu
                 405                 410                 415

Gln Gly Gly Ile Lys Asp Leu Ser Lys Glu Glu Arg Leu Trp Glu Val
             420                 425                 430

Gln Arg Ile Leu Thr Ala Leu Lys Arg Lys Leu Arg Glu Ala Lys Arg
         435                 440                 445

Gln Glu Cys Glu Thr Lys Ile Ala Gln Glu Ile Ala Ser Leu Ser Lys
450                 455                 460

Glu Asp Val Ser Lys Glu Glu Met Asn Glu Asn Glu Glu Val Ile Asn

```
                465                 470                 475                 480
Ile Leu Leu Ala Gln Glu Asn Glu Ile Leu Thr Glu Gln Glu Leu
                    485                 490                 495

Leu Ala Met Glu Gln Phe Leu Arg Arg Gln Ile Ala Ser Glu Lys Glu
            500                 505                 510

Glu Ile Glu Arg Leu Arg Ala Glu Ile Ala Glu Ile Gln Ser Arg Gln
        515                 520                 525

Gln His Gly Arg Ser Glu Thr Glu Glu Tyr Ser Ser Glu Ser Glu Ser
    530                 535                 540

Glu Ser Glu Asp Glu Glu Glu Leu Gln Ile Ile Leu Glu Asp Leu Gln
545                 550                 555                 560

Arg Gln Asn Glu Glu Leu Glu Ile Lys Asn Asn His Leu Asn Gln Ala
                565                 570                 575

Ile His Glu Glu Arg Glu Ala Ile Ile Glu Leu Arg Val Gln Leu Arg
            580                 585                 590

Leu Leu Gln Met Gln Arg Ala Lys Ala Glu Gln Gln Ala Gln Glu Asp
        595                 600                 605

Glu Glu Pro Glu Trp Arg Gly Gly Ala Val Gln Pro Arg Asp Gly
    610                 615                 620

Val Leu Glu Pro Lys Ala Ala Lys Glu Gln Pro Lys Ala Gly Lys Glu
625                 630                 635                 640

Pro Ala Lys Pro Ser Pro Ser Arg Asp Arg Lys Glu Thr Ser Ile
                645                 650                 655

<210> SEQ ID NO 24
<211> LENGTH: 21
<212> TYPE: DNA
<213> ORGANISM: artificial sequence
<220> FEATURE:
<223> OTHER INFORMATION: scrambled sequence used with phosphorothioated
      DNA

<400> SEQUENCE: 24
catcgaaatc gttgcagtta c                                                 21
```

THERAPIES FOR CANCER USING RLIP76

CROSS-REFERENCES TO RELATED APPLICATIONS

This application is a continuation of U.S. application Ser. No. 11/264,910, filed Nov. 2, 2005, which is a continuation-in-part of prior U.S. application Ser. No. 10/714,506, filed Nov. 13, 2003, which claims the benefit of U.S. Provisional Patent Application No. 60/425,917, filed Nov. 13, 2002, all of which are incorporated herein by reference for all purposes. This application is also a continuation-in-part of prior U.S. application Ser. No. 10/713,578, filed Nov. 13, 2003, which claims the benefit of U.S. Provisional Patent Application No. 60/425,814, filed Nov. 13, 2002, both of which are incorporated herein by reference for all purposes.

STATEMENT REGARDING FEDERALLY SPONSORED APPLICATIONS

The U.S. Government has a paid-up license in this invention and the right in limited circumstances to require the patent owner to license others on reasonable terms as provided for by the terms of Grant No. NIH 2-R01-CA77495, Grant No. NIH CA 104661.

REFERENCE TO A SEQUENCE LISTING

This application incorporates by reference sequence listing material included on computer readable form and identified as 124263-1040 RLIP.ST25.txt saved on Nov. 2, 2005, in ASCII readable form.

BACKGROUND OF THE INVENTION

The present invention relates to improved anti-cancer therapies, particularly one targeted towards cells expressing high levels of a ral interacting protein, RLIP76.

Current therapies for human cancers are generally unsatisfactory because of a high rate of failure and excessive side-effects. Side effects are generally significant and result, in part, because few current therapies are targeted to cancerous cells alone. There remains a need to identify targeted therapies that eliminate only cancerous cells and not healthy cells.

SUMMARY OF THE INVENTION

The present invention solves problems associated with current therapies for cancerous cells or those that undergo uncontrolled cell growth (e.g., cancerous, tumorigenic and malignant cells). In particular, the present invention provides compositions for inhibiting and/or depleting RLIP76.

As provided herein, RLIP76 is a membrane associated protein and a critical as well as predominant regulator of transport in cancerous cells or those undergoing uncontrolled cells growth. Targeting therapies against RLIP76 directly effects RLIP76 transport activity and reduces the number and/or potency of such cells undergoing uncontrolled cell growth in subjects having such uncontrolled and growing cells.

The present invention provides for compositions that target RLIP76 and reduce the number and/or potency of cells undergoing uncontrolled cell growth. Compositions comprise a region homologous to a portion of a ralA binding protein 1, wherein the region neighbors a membrane-associated portion of the ralA binding protein 1, reduces transport activity and membrane association of ralA binding protein 1 and kills cells undergoing uncontrolled cell growth in a subject that has cells undergoing uncontrolled cell growth.

Compositions of the present invention include an internal peptide region of RLIP76 to be used as bait in screens of chemical libraries for synthetic and naturally occurring organic chemicals and compounds with an ability to reduce the number and/or potency of cells undergoing uncontrolled cell growth. The identified chemicals and compounds are those acting as specific inhibitors of RLIP76 activity (e.g., found to reduce the number and/or potency of cells undergoing uncontrolled cell growth). As such, the present invention provides for compositions that are improved therapies for cancers, malignancies, and tumorigenic or uncontrolled growth cells that express RLIP76.

In one form, the present invention provides for a region recognizing a ralA binding protein 1, wherein the region further comprises SEQ ID NO:28 and modified variants thereof.

In other forms, the present invention provides for compositions and methods of using such compositions as SEQ ID NO: 3 to SEQ ID NO:19 and SEQ ID NO:21. Such compositions, in various forms to be used to identify compounds as medicines for cancers, malignancies and tumors and for reducing the number and/or potency of cells undergoing uncontrolled cell growth.

Those skilled in the art will further appreciate the above-noted features and advantages of the invention together with other important aspects thereof upon reading the detailed description that follows in conjunction with the drawings.

BRIEF DESCRIPTION OF THE DRAWINGS

For more complete understanding of the features and advantages of the present invention, reference is now made to the detailed description of the invention along with the accompanying figures, wherein:

FIG. 3 depicts a depletion of RLIP76 expression in malignant and non-malignant cells using RLIP76 si-RNA;

FIG. 4 depicts a time dependent effect of RLIP76 si-RNA in malignant and non-malignant cells;

FIGS. 6 A and B-J depict antineoplastic effects of RLIP76 inhibition or depletion in mouse melanoma in which (A) shows tumor measurements pooled from control animals, including PBS, pre-immune IgG, scrambled siRNA antisense injection (circle), versus treated animals, including anti-RLIP76 IgG, RLIP76 siRNA, RLIP76 phosphorothioate antisense injection (square), and (B)-(J) show photographs of representative animals taken at eight days after treatment.

FIG. 7 is a diagram of a method of identifying inhibitors or RLIP76 transport activity.

DETAILED DESCRIPTION OF THE INVENTION

Figure 1:
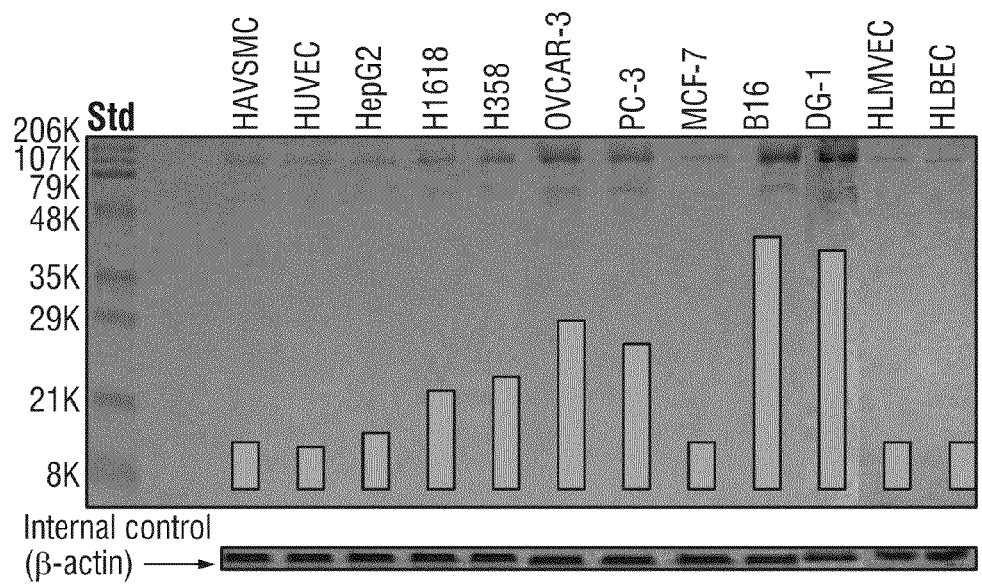
FIG. 1 depicts comparison of RLIP76 levels in cultured malignant vs. non-malignant cells.

Although making and using various embodiments of the present invention are discussed in detail below, it should be appreciated that the present invention provides many inventive concepts that may be embodied in a wide variety of contexts. The specific aspects and embodiments discussed herein are merely illustrative of ways to make and use the invention, and do not limit the scope of the invention.

In the description which follows like parts are marked throughout the specification and drawing with the same reference numerals, respectively. The drawing figures are not necessarily to scale and certain features may be shown exaggerated in scale or in a somewhat generalized or schematic form in the interest of clarity and conciseness.

The following are abbreviations that may be used in describing the present invention: RLIP, ral interacting protein; MDR, multi-drug resistance; GS-E, glutathione-electrophile conjugates; phenyloin, PHE; carbamazepine, CBZ.

Current antineoplastic therapies for human malignancies are limited by the occurrence of significant normal tissue toxicities due to inherent relatively non-specific genotoxic or signaling effects. Attempts to improve antineoplastic therapies have focused on identifying targets which are preferentially expressed in cancer cells, which when inhibited cause apoptosis in malignant cells while sparing cells of normal tissues. Delineation of differentially expressed signaling proteins that are responsible for un-regulated growth and suppression of normal apoptotic pathways has led to the identification of numerous potential targets. While new agents have emerged, such as antibodies including rituximab (anti-CD20 antibody for lympho-proliferative disorders), trastuzumab (anti-Her-2/neu antibody for breast cancer) and small molecules including imatinib mseylate (Bcr-Abl kinase inhibitor for chronic myelogenous leukemia) and erlotinib (tyrosine kinase inhibitor for a variety of solid tumors), their overall efficacy remains limited, because of their limited effectiveness in only a small fraction of patients with such malignancies or because of clonal selection of cancer cells inherently refractory to such therapies. Thus, development of new targeting molecules and discovery of new targets remains critical.

RLIP76 (also referred to herein as RALBP1) represents a novel target for cancer therapy not only because of its involvement in the rate-controlling step in glutathione (GSH)-mediated metabolism of electrophilic or oxidant chemicals often used as anti-neoplastic agents, but also because of its apparent linkage to key signaling pathways known to be crucial for the survival, proliferation, and motility of malignant cells. The present inventors have recently demonstrated that lack of RLIP76 in knockout mice leads to loss of nearly ⅘ of total GSH-conjugate (GS-E) as well as anthracycline-transport activity, and widespread changes in GSH-linked antioxidant enzymes (as disclosed, e.g., in Awasthi S, et al. Cancer Res 2005; 65:6022-8). RLIP76$^{-/-}$ mice develop a characteristic sensitivity to stress, particularly to ionizing radiation. These and other studies by the inventors in cell culture systems implicate RLIP76 as a part of stress-defenses (as disclosed, e.g., in Yang, et al., J Biol Chem 2003; 278:41380-88). In particular, the inventors have determined that inhibition of RLIP76 transport function using antibodies to a cell-surface epitope or depletion of RLIP76 using si-RNA uniformly causes apoptosis in a variety of histological types of cancers (as disclosed, e.g., in Awasthi, et al., Int J Oncol 2003; 22:713-20; Awasthi, et al., Int J Oncol 2003; 22:721-32; Yadav, et al., Biochemistry 2004; 43:16243-53; Struckler, et al., Cancer Res 2005; 65:991-8).

The present invention provides clinical applicability of RLIP76 as a target for anti-cancer therapy. The present invention confirms that there is a greater dependence on RLIP76 in cancer cells, due to greater expression of the protein in such cells. The present invention shows that this dependence translates to a greater susceptibility of cancer cells to agents that deplete RLIP76; hence, RLIP76 is a powerful target a broad-spectrum anti-cancer therapy.

Anti-RLIP agents, those that reduce and inhibit protein function or deplete expression of the protein are provided herein. Such agents include anti-RLIP76 IgG, si-RNA and anti-sense DNA oligonucleotides. With the present invention, it is demonstrated that because RLIP76 is expressed to a greater degree in malignant cells and RLIP76 inhibition or depletion causes preferential toxicity towards malignant cells, anti RLIP agents exert significant antineoplastic effects in the malignant cells.

The inventors, Sanjay Awasthi and Sharad S. Singhal, of the present invention have recently described a novel non-ABC transporter that appears to be multispecific as a Ral interacting protein (see U.S. application Ser. No. 10/714,506; U.S. application Ser. No. 10/713,578; each incorporated herein by reference). As used herein, this transporter is referred to RLIP76 or RalBP1. The official human genome name for the protein is RALBP1 (SEQ ID NO:1; and SEQ ID NO:22 for the coding sequence). RLIP76 is a modular multifunctional and modular protein found ubiquitously in many species from *Drosophila* to humans. It is encoded in humans on chromosome 18p11.3 by a gene with 11 exons and 9 introns. The protein product, also known as ralA binding protein 1, is typically a 76 kDa (SEQ ID NO:2; and SEQ ID NO:23 for the coding sequence) protein; however, splice-variants including a 67 kDa peptide and a longer 80 kDa or 102 kDa peptide, cytocentrin, have also been identified.

Malignant cells contain a greater quantity of antigenically detectable RLIP76 as shown in the Table and in FIG. 1 in which RLIP76 obtained from various cell lines (of different origin) was quantitated (not all purification data shown). The Table and FIG. 1 shows there to be greater RLIP76 in malignant cells as compared with non-malignant cells. Total RLIP76 protein was purified from membrane fraction of several malignant cell lines, including human small cell lung cancer (SCLC; H1618), non-small cell lung cancer (NSCLC; H358), ovarian (OVCAR-3), breast (MCF-7), prostate (PC-3), liver (HepG2), melanoma (DG-1), mouse melanoma (B16-F1) and non-malignant human cell lines of endothelial (HUVEC, HLMVEC), epithelial (HLBEC), and aortic smooth muscle (HAVSMC) origin. Purification folds of 120 to 153 were observed, and single protein band of intact RLIP76 were seen in SDS PAGE, which were recognized by purified polyclonal rabbit-anti-human RLIP76 antibodies in Western blot analyses. Antibodies were not non-cross-reactive with other proteins including PgP or MRP-1. No significant contamination was observed in the Western blots. Representative purified protein data, quantified by ELISA, are shown in TABLE 1. Western blot analyses of crude membrane fraction from each cells with lanes loaded with equal amount of crude protein (200 μg) are shown in FIG. 1. RLIP76 was purified by DNPSG-affinity as described previously by the inventors (Singhal, et al., Int J Oncol 2003; 22:365-75). Briefly, cells were pelleted and washed with a balanced salt solution (138 mM NaCl, 5 mM KCl, 0.3 mM KH$_2$PO$_4$, 0.3 mM Na$_2$HPO$_4$, 4 mM NaHCO$_3$, and 5.6 mM glucose, pH 7.4). Cells were lysed in a lysis buffer (10 mM Tris-HCl, pH 7.4, containing 1.4 mM BME, 0.1 mM PMSF, 0.05 mM BHT and 0.1 mM EDTA) followed by sonication and recovery of pellets in lysis buffer containing 0.25% polidocanol. After incubation for 4 hours in the cold, samples were centrifuged and supernatants applied to DNP-SG Sepharose-affinity column. Homogenous RLIP76 was obtained using methods known to one of ordinary skill in the art.

TABLE

RLIP76 Protein and transport activity in malignant and non-malignant cell lines.

| | RLIP76 Protein | | Transport Activity | |
|---|---|---|---|---|
| | $\mu g/10^8$ cells | % of total protein | (pmol/min/mg) | |
| | | | DOX | DNP-SG |
| MALIGNANT CELLS | | | | |
| B16 (mouse melanoma) | 71 ± 6 | 0.8 | 443 ± 34 | 1796 ± 145 |
| DG-1 (human melanoma) | 63 ± 5 | 0.8 | 384 ± 28 | 1562 ± 112 |
| OVCAR-3 (human ovary) | 53 ± 3 | 0.7 | 298 ± 23 | 1194 ± 122 |
| PC-3 (human prostate) | 46 ± 3 | 0.6 | 211 ± 26 | 893 ± 66 |
| H358 (human lung, NSCLC) | 36 ± 3 | 0.6 | 180 ± 15 | 695 ± 56 |
| H1618 (human lung, SCLC) | 32 ± 3 | 0.5 | 96 ± 12 | 361 ± 41 |
| MCF-7 (human breast) | 15 ± 1 | 0.2 | 36 ± 3 | 105 ± 7 |
| HepG2 (human liver) | 17 ± 1 | 0.3 | 55 ± 5 | 167 ± 14 |
| NON-MALIGNANT CELLS | | | | |
| HLMVEC (human lung endothelium) | 19 ± 2 | 0.3 | 40 ± 5 | 136 ± 14 |
| HLBEC (human lung epithelium) | 22 ± 2 | 0.4 | 46 ± 4 | 150 ± 20 |
| HAVSM (human aorta smooth muscle) | 15 ± 1 | 0.3 | 40 ± 6 | 125 ± 10 |
| HUVEC (human umbilical endothelial) | 14 ± 1 | 0.2 | 36 ± 4 | 113 ± 12 |

Transport activity of RLIP76 is greater in malignant cells as determined by membrane vesicles prepared from plasma membrane fractions from each cell line, enriched for inside-out vesicles (IOVs) by wheat-germ agglutinin affinity chromatography as previously described by the inventors (see, e.g., Awasthi, et al., Int J Cancer 2004; 112:934-42). Results of measurements of ATP-dependent transport of $^{14}$C-doxorubicin (DOX) as well as $^{3}$H-dinitrophenyl S-glutathione (DNP-SG) using a standardized 96 well-plate transport assay revealed greater transport of both substrates in cells containing greater amount of RLIP76 protein. The Table shows the general correlation between RLIP76 protein level and transport activity. The greatest transport activity was found in melanoma cells with transport activity greater than in malignant than non-malignant cells. Low expression of RLIP76 in MCF-7 and HepG2 correlated with lower transport rate in the crude-membrane vesicles. Total DOX or DNP-SG transport rate correlated with either RLIP76 protein amounts (Table) or RLIP76 ATPase activity (data not shown). ATPase activity was measured using aliquots of protein fraction containing 1 to 10 μg protein added to a 0.5 mL reaction mixture (50 mM Tris-HCl pH 7.4, 10 mM $MgCl_2$, 2 mM EGTA, 0.8 mM sodium phosphate, 2.8 mM β-mercaptoethanol, and 1 mM ouabain) that incubated for 5 minutes at 37° C. Each reaction was initiated with 1.6 mM γ-$^{32}$P-ATP with or without 0.12 mM DNP-SG or 0.01 mM DOX. After 60 minutes each reaction was terminated by addition of a 2.5 ml cold mixture of 1 M perchloric acid and 5% ammonium molybdate in water (4:1) followed by extraction with a 2.5 mL mixture of isobutanol-benzene (1:1). Radioactivity was quantified in the organic phase to determine cleaved terminal phosphate. RLIP76 activity was calculated by subtracting background counts obtained in the absence of protein from those obtained in the presence of protein. RLIP76 activity was calculated by subtracting the activity seen in the absence of DOX or DNP-SG from that seen in its presence. Each assay was performed in triplicate.

Crude membrane vesicles (inside-out vesicles or IOVs) were prepared from non-malignant cells (HAVSMC, HLBEC, HLMVEC and HUVEC) and cancer cells (SCLC, NSCLC, DG-1 human melanoma, mouse B16 melanoma, MCF7, HepG2, PC-3 and OVCAR-3) identified in the Table using procedures known in the art (see, e.g., Awasthi, et al., Clin Invest 1994; 93:958-65; Awasthi, et al., Biochemistry 2000; 39:9327-34). Transport studies in IOVs were performed by method known in the art (see, e.g., Awasthi, et al., Int J Cancer 2004; 112:934-42) in which heat-inactivated IOVs were used as negative controls.

Figure 2:
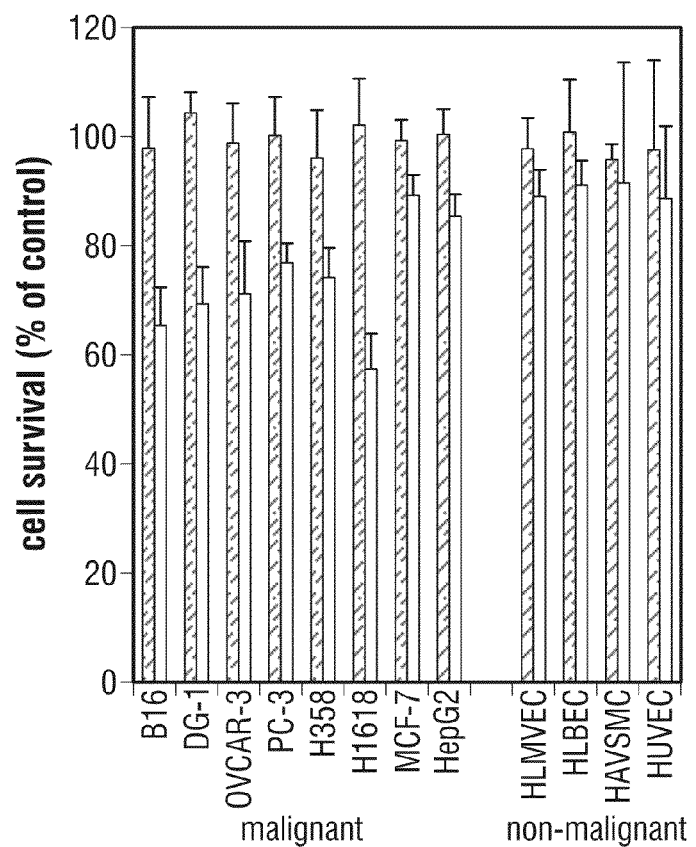
FIG. 2 depicts effects of pre-immune IgG (dark bars) and anti-RLIP76 IgG (white bars) (37 µg/ml final) on cell survival as determined by MTT assay.

RLIP76 inhibition or depletion caused preferential cytotoxicity in malignant cells. RLIP76 was inhibition by anti-RLIP76 IgG or via depletion using si-RNA (si-RNA[508-528]) targeted to a specific identified region of RLIP76. Varying concentrations of either inhibitor were used in an MTT assay. Maximum inhibition was observed near 40 μg/mL by MTT assay (data not shown). Anti-RLIP76 demonstrated greater cell kill in malignant cell lines (p<0.01); pre-immune IgG caused no significant cell kill. Maximal susceptibility was observed with the melanoma cell lines and the SCLC cell line (FIG. 2). Cell density measurements were performed using a hemocytometer to count dye-excluding cells resistant to staining with trypan blue. Approximately $2 \times 10^4$ cells were plated into each well of 96-well flat-bottomed microtiter plate 24 hours prior to addition of medium containing varying concentrations of either pre-immune serum or anti-RLIP76 IgG (0-100 μg/mL final concentration). MTT assays were carried out 96 hours later using methods known in the art (see, e.g., Awasthi, et al., Int J Cancer 1996; 68:333-9) with eight replicate wells per measurement and three separate experiments to determine $IC_{50}$. Measured absorbance values were directly linked with a spreadsheet for calculation of $IC_{50}$, defined as the concentration that reduced formazan formation by 50%.

si-RNA[508-528] was targeted to region of RLIP76 and corresponds closely with a region spanning amino acids 171-185 (nucleotide 510-555 starting from 1 AUG codon in the open reading frame) in the N-terminal region of RLIP76 si-RNA[508-528] is particularly novel in that it lacks homology with other proteins or nucleotide sequences. More details regarding its preparation and described later.

Figure 5:
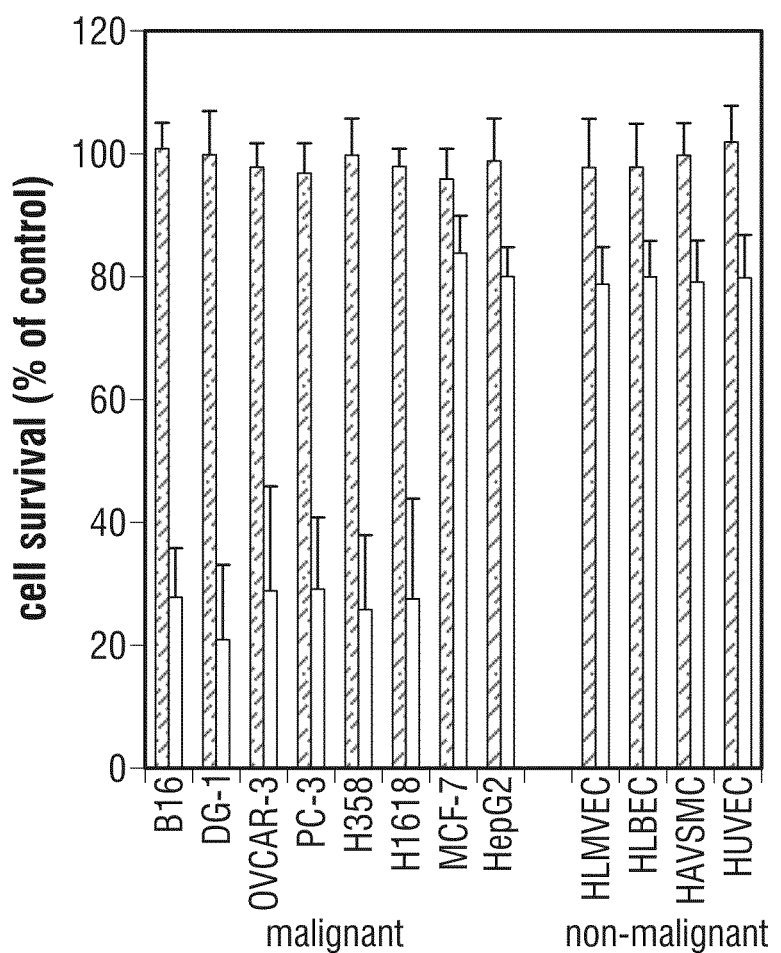
FIG. 5 depicts MTT assays for malignant and non-malignant cells performed 48 hours after treatment with si-RNA in which grey bars show scrambled si-RNA white bars show RLIP76 si-RNA.

With RLIP76 si-RNA[508-528] (at a concentration of 20 μg/ml), there was a complete depletion of RLIP76 protein after 24 to 48 hours. Non-malignant cells were less sensitive to RLIP76 depletion as compared with malignant cells. For example, 10 μg/ml si-RNA affected B16 melanoma cells significantly more than HLMVEC (FIG. 3). The time for maximal depletion of RLIP76 protein was also determined by exposing cells to 40 µg/ml RLIP76 si-RNA$^{508-528}$ and performing Western-blot analyses after varying time of exposure. The relative resistance of non-malignant cells to RLIP76 depletion by si-RNA is shown in FIG. 4, where several non-malignant cell lines (HLMVEC, HLBEC, HAVSM, and HUVEC) were less affected with respect to RLIP76 protein at 24 and 48 h as compared with the malignant cell lines (B16, DG1, Ovcar-3, PC-3, H358, and H1618). MTT cytotoxicity assay, RLIP76 si-RNA$^{508-528}$ killed the malignant cells in a concentration dependent manner with relative sparing of the non-malignant cells (FIG. 5). The relative efficacy of cell kill was greater with the si-RNA (FIG. 5; FIG. 2D) as compared with anti-RLIP76 IgG (FIG. 4; FIG. 2A). TUNEL assay for apoptosis was performed with anti-RLIP76 IgG showing data consistent with those observed for the MTT assay in which with greater apoptosis was found in malignant cells (data not shown).

TUNEL assays were measured on adherent cells and floating cells. For adherent cells, approximately 1×10$^6$ cells were placed into 12-well plates containing coverslips and allowed to incubate with either pre-immune serum or anti-RLIP76 IgG (37 µg/ml final concentration) for about 24 hours. For floating cells, approximately 1×10$^6$ cells were grown for 24 hours in 12-well plates then incubated with either pre-immune serum or anti-RLIP76 IgG (37 µg/ml final concentration) before transferring to histological slides. Apoptosis was then determined by labeling DNA fragmentations using a terminal deoxynucleotidyl-transferase dUTP end labeling method as know in the art. Free 3'-OH DNA ends (characteristic of DNA fragmentation) were labeled using a reaction catalyzed by terminal deoxynucleotidyl-transferase (TdT). Samples were analyzed by laser scanning fluorescence microscope. Apoptotic cells showed green fluorescence and characteristic cell shrinkage.

Anti-RLIP76, si-RNA or antisense DNA caused complete regression of B16 melanoma in mice. C57B mice were injected on their flanks with 1×10$^6$ B16-F1 melanoma cells and tumors were measured by calipers daily. When the surface area of the tumor (product of bi-dimensional measurements) exceeded 40 mm$^2$ (day 11), animals were injected intraperitoneally with 100 µl diluent alone (phosphate buffered saline, PBS) or the same volume of diluent containing 200 µg anti-RLIP76 IgG, RLIP76 si-RNA$^{508-528}$, or RLIP76 phosphorothioate antisense$^{508-528}$. Additional control animals were injected with pre-immune IgG, scrambled si-RNA or antisense si-RNA. Tumors regressed completely in all animals treated with any inhibitor of RLIP76, whereas uncontrolled growth was observed in the control groups (FIG. 6A). FIG. 6B-6J show representative images of animals in all treatment groups taken eight days after treatment. Animal data demonstrates the dramatic in vivo effect an anti-RLIP76 agent has on tumor regression.

The region spanning amino acid residues 171-185 (nucleotide 510-555 starting from 1 AUG codon in the open reading frame) in the N-terminal region of RLIP76 was chosen as the target region for synthesis of phosphorothioate DNA. The oxygen in the backbone of the DNA molecules was replaced by sulfur in each phosphate group, which makes the DNA backbone resistant to nucleases. However, the macromolecule remains electrically charged, impeding its passage across cell membrane. Selected DNA sequence was subjected to blast-search (NCBI database) against EST libraries, to ensure that only the selected gene was targeted. Chemically synthesized phosphorothioate DNA in desalted form was purchased from Biosynthesis Inc. A 21-nucleotide long scrambled phosphorothioate DNA was used as a control. The scrambled DNA sequence was not homologous with RLIP76 cDNA in a blast-search against RLIP76. The targeted cDNA sequence (SEQ ID NO: 19 or AAGAAAAAGCCAAT-TCAGGAGCC) corresponded to nucleotides 508-528. A corresponding phosphorothioated DNA sequence was GGCTC-CTGAATTGGCTTTTTC (SEQ ID NO: 20). The sequence of the scrambled DNA was CATCGAAATCGTTGCAGT-TAC (SEQ ID NO: 21). Transfection of phosphorothioate DNA was performed using a transfection kit known in the art; cells were assayed for silencing 24 hours after transfection.

C57 BL/6 mice were obtained and colonies bred in accordance with standard institutional protocols. In brief, twenty-one 16-week-old mice were divided into seven groups of 3 animals (PBS control; pre-immune IgG control; scrambled si-RNA control; scrambled phosphorothioate oligonucleotide control; anti-RLIP76 IgG, RLIP76$^{508-528}$ si-RNA, and RLIP76$^{508-528}$ phosphorothiate antisense oligonucleotide). Each of 21 animals was injected with 2×10$^6$ B16 mouse melanoma cell suspensions in 100 µl of PBS, subcutaneously. Animals were examined daily for signs of tumor growth. Treatment was administered when the tumor surface area exceeded 45 mm$^2$ (at day 11). Treatment consisted of 200 µg in 100 µL PBS of either anti-RLIP76 IgG, RLIP76$^{508-528}$ si-RNA, or RLIP76$^{508-528}$ phosphorothioate antisense oligonucleotide. Control groups were 200 µg/100 µl of either pre-immune IgG, scrambled si-RNA, or scrambled phosphorothioate antisense, or diluent (PBS) alone. Tumors were measured in two dimensions using calipers on days 1, 3, 5, 7, 9, 11, 13, 15, 17 and 20.

The present invention demonstrates the over-expression of RLIP76 in most malignant cells that undergo uncontrolled cells growth as compared with non-malignant cells that do not undergo uncontrolled cell growth. With greater RLIP76 expression, there was increased transport activity of RLIP76 (as demonstrated using transport agents such as DOX or DNP-SG). With greater protein expression there was also an increased dependence on RLIP76 protein as a transport molecule. The present invention also provides for an in vivo effect of targeted anti-RLIP agents in cells undergoing uncontrolled cell growth. Regression of an established melanoma nodule upon administration of a single dose of an anti-RLIP76 agent only 11 days after tumor implantation was observed in mice. Such results are unlike any observed with other anti-cancer therapies. In culture, si-RNA administration was superior to that observed with anti-RLIP76 IgG; in vivo, treatments appeared to provide similar efficacy when equivalent doses were administered. RLIP76 antibody effects may relate to contributions of antibody-dependent cellular cytotoxicity effects.

Accordingly, the present invention indicates that increased RLIP76 expression is associated with clinical cancerous growth (uncontrolled cells growth). As such, inhibition of RLIP76 offers a targeted solution to eradicate tumorigenic or malignant cells. RLIP76 appears to be a significant transporter in such cells and the activity of RLIP76 appears to be directly involved in uncontrolled cells growth, malignancy and tumorigenicity.

To specifically target unwanted tumorigenic or malignant cells, the present invention provides for compositions that antagonize, inhibit or deplete RLIP76 (e.g., inhibit RLIP76 transport activity); such compositions being new and important antineoplastic agents to be used alone or in combination with existing therapies. The antagonists include compounds that interact with a cell-surface domain of RLIP76 that directly affects RLIP76 transport activity. Suitable compositions include those molecules that inhibit, reduce or deplete transport activity of RLIP76 and may be identified as described below.

The inventors have recently reported several surface epitope regions of RLIP76 when membrane bound to cells. The surface epitope region was found necessary for optimal transport activity of RLIP76 as described by Yadav et al., Biochemistry 2004; 43:16243-53, herein incorporated by reference. One surface epitope region comprises on or about amino acids (aa) 154 to 219 (SEQ ID NO:3 and conservatively modified variants, thereof, including deletions of 1 to 5 residues at the C-terminus and or N-terminus). Another surface epitope region comprises on or about amino acids 171 to 185, corresponding to an aa sequence KPIQEPEVPQIDVPN (SEQ ID NO:4 and conservatively modified variants, thereof, including deletions of 1 to 5 residues at the C-terminus and or N-terminus). Such surface epitope regions are not only necessary for optimal transport activity, they are also useful portions of the protein for the identification of inhibitors of RLIP76 transport activity. For example, a deletion mutant protein lacking amino acids 171 to 185 resulted in loss of hydrophobicity of the protein, decreased association of the protein with artificial liposomes, and decreased transport activity. In addition, cells transfected with 171-185 si-RNA (SEQ ID NO:5) resulted in loss of cell surface expression (e.g., decreased membrane association).

Accordingly, the present invention identifies regions of the protein acting as surface epitopes and capable of providing antagonists (e.g., inhibitors) for RLIP76. Antagonists, as identified herein, include antibodies directed against one or more surface epitope region (e.g., humanized monoclonal antibody), si-RNA sequences directed against one or more surface epitope regions, as well as small molecules found using chemical library screenings against peptides containing one or more surface epitope regions.

In one form, surface epitope regions and their variants, as identified herein, are synthesized and immobilized on an inert support material and used to screen chemical libraries for compounds that bind this peptide. Suitable methods for chemical library screening are known to one of ordinary skill in the art. The compounds identified by the screening process are tested in a secondary screen that included a liposomal transport assay to determine efficiency of inhibition of RLIP76. RLIP76 inhibitors are also tested in animals alone and in combination with existing anti-seizure medicines in order to evaluate safety and efficacy of each identified inhibitor.

SEQ ID NO:3 and SEQ ID NO:4 were identified from a series of deletion mutant proteins to RLIP76 (data not shown; see Yadav et al., 2004). In brief, a series of deletion mutants were prepared by PCR-based site-directed mutagenesis using a clone of the full length RLIP76 in an expression vector [pET30a(+)] as template and upstream primer 5' GCGGATC-CATGACTGAGTGCTTCCT (SEQ ID NO:5: BamH1 restriction site is underlined) and downstream primer 5'CCGCTCGAGTAGATGGACGTCTCCTTCCTATCCC (SEQ ID NO:6; XhoI restriction site underlined). Mutants included those having deletions of amino acids 203 to 219 (del 203-219), 154 to 171 (del 154-171), 171 to 185 (del 171-185), 154 to 219 (del 154-219), 415 to 448 (del 415-448) and 65 to 80 (del 65-80). The mutagenic primers for del 203-219: 5' GTAGAGAGGACCATGGTAGAGAAG-TATGGC 3' (SEQ ID NO: 7) with its reverse complement); for del 154-171:5' AAGAAGTCAAAAGACAAGCCAAT-TCAGGAG (SEQ ID NO: 8; with its reverse complement); for del 171-185: 5'GAAGAAAAAGAAACTCAAAC-CCATTTTT 3' (SEQ ID NO: 9; with its reverse complement); for del 154-219: 5' GAAGAAGTCAAAAGACGTA-GAGAAGTATGGC 3' (SEQ ID NO: 10; with its reverse complement; for del 415-448: 5' GAATTGTTTACATCGA-CAGGAGTGTGAAACC (SEQ ID NO: 11; with its reverse complement); and for del 65-80: 5' GTGTCTGATGATAG-GACTGAAGGCTATG 3' (SEQ ID NO: 12 and its reverse complement).

The template and each deletion mutant was expressed in E. coli and after bacterial lysis (with e.g., 1% (w/v) $C_{12}E_9$ in lysis buffer), the protein was extracted by methods known to one of ordinary skill in the art. For the full length protein and the deletion mutants, one method of protein purification to nearly homogeneity from bacterial extracts used DNP-SG affinity resins (for full description see in Awasthi, et al. Biochemistry 2000:39:9327-9334, herein incorporated by reference). Introduction of deletions specified above in wild type RLIP76 did not affect the affinity of protein with DNP-SG; all deletion mutants could be purified by DNP-SG affinity chromatography. Protein purity was ascertained by SDS-PAGE, Western blot and amino acid composition analysis using methods know in the art and as described in Awasthi et al. 2000. The authenticity of the mutation and the absence of other fortuitous mutations were confirmed by DNA sequencing for each of the deletion mutants.

Full-length RLIP76 (wt-RLIP76) and deletion mutants (del 203-219, del 154-171, del 171-185, del 154-219, del 65-80, del 415-448 and del 65-80) were expressed as recombinant (rec) proteins in E. coli (using pET30a(+) plasmid under the control of the lac UV5 promoter. Single bacterial colonies were used to induce protein expression. To facilitate extraction of the rec-RLIP76 and its various deletion mutants, bacterial lysates were collected, sonicated, and incubated. After incubation, each reaction mixture was centrifuged and the supernatant fraction was obtained as a cytosol fraction and the pellet was the membrane fraction. The membrane fraction was resuspended in 1% polidocanol (a non-ionic detergent) sonicated again, incubated and collected in the supernatant after centrifugation.

When extracted in detergent-containing buffer, the ratio of RLIP76 in the detergent/aqueous extracts was found to be 2.5 for the wild-type protein, but decreased to 0.7 in the mutant in which aa 154-219 (SEQ ID NO:4) were deleted (data not shown; see Yadav et al., 2004). Deletion of only one segment of this region (del 171-185 or SEQ ID NO:3) alone resulted in a significant decrease in this ratio to 1.0. For the mutants with deletions within the region from aa 154-219, loss of hydrophobicity correlated with decreased incorporation of mutants into artificial liposomes, and decreased transport activity. The data indicates that the 154-219 region of RLIP76 significantly affects protein partitioning between cytosol and membranes; Residues 171-185 contribute significantly to this effect.

Functional reconstitution of purified RLIP76 from E. coli for transport studies was performed using methods known to one of ordinary skill in the art, an example of which is described in Awasthi, et al. 2000. The degree of incorporation of wild-type as well as mutant RLIP76 into artificial liposomes was assessed by measuring RLIP76 after centrifugation (pellet and supernatant of prepared liposomes) by ELISA assay using anti-RLIP76 antibodies. Measurement of the transport of a cationic agent, doxorubicin (DOX), in the reconstituted liposomes was performed using methods known to one of ordinary skill in the art, an example of which is described in Awasthi, et al. 2000. The ATP-dependent uptake of $[C^{14}]$-DOX (specific activity $8.4 \times 10^4$ cpm/nmol) was determined by subtracting the radioactivity (cpm) of the control without ATP from that of the experimental containing ATP. Transport of DOX was calculated in terms of pmol/min/mg protein. The transport of $[^3H]$-DNP-SG (specific activity $3.2 \times 10^3$ cpm/nmol) was measured using methods known to one of ordinary skill in the art, an example of which is described in Awasthi, et al. 2000.

The majority (87%) of total wild-type RLIP76 was found in the pellet fraction, incorporated into the proteoliposomes. Deletion of aa 203-219 or 154-171 decreased incorporation slightly (to 83 and 80%, respectively). Deletion of aa 171-185 significantly effected incorporation of the protein into proteoliposomes (64%) as did deletion of residues 154-219, with only 33% of total protein found incorporated into proteoliposomes. Deletions affecting the ATP-binding sites (aa 65-80 and aa 415-448) had no significant effect on the amount of protein incorporated into proteoliposomes. Thus region 154-219 is an important determinant of membrane insertion.

For ATP-dependent transport of molecules across the proteoliposomes, transport was significantly decreased (21%) in the mutant lacking aa 154-171 (27.6 versus 21.7 nmol/min/mg for transport of DOX by the full length RLIP76 versus the deletion mutant, $p<0.05$). Deletion of aa 171-185 resulted in approximately 40% loss of transport activity for DOX and a similar loss (35%) in transport activity for dinitrophenyl S-glutathione (DNP-SG). Deletion of the entire 154-219 region resulted in further significant loss (50%) of transport activity for both DOX and DNP-SG. Because deletion of ATP-binding site regions did not affect partitioning of the mutants between cytosol and membrane, the observed decrease in transport activity of deletion mutant aa 154-219 is believed due to loss of protein association with the membrane because of its decreased partitioning in the membrane.

The effect in eukaryotes of losing surface epitope regions spanning residues 171-185 (SEQ ID NO:4) or 154-219 (SEQ ID NO:3) was similar to that described above (data not shown; see Yadav et al., 2004). When H358 cells were transfected with an empty vector (pcDNA3.1) or a vector containing either full length RLIP76 or its deletion mutants lacking aa 171-185 or aa 154-219, membrane association of RLIP76 was significantly reduced in cells transfected with the deletion mutants, as analyzed by Western blots. Hence, the aa 154-219 region is a determinant of the membrane association of RLIP76 and it is independent of whether the protein is expressed in eukaryotes or prokaryotes. Immuno-histochemistry studies using anti-RLIP76 antibodies raised against full-length RLIP76 were performed with live, unfixed H358 wild-type cells and examined by confocal laser microscopy and showed a staining pattern consistent with cell-surface localization. RLIP76 co-localized with another protein, her2/neu, known to have a cell-surface domain. Anti-RLIP76 antibody was detected using a rhodamine red-x-conjugated secondary antibody, and anti-her2/neu antibody using an FITC tagged secondary antibody. Cell-surface epitopes were recognized by both anti-RLIP76 and her2/neu antibodies which co-localized in unfixed cells indicating that RLIP76 had cell-surface epitopes just like her2/neu.

H358 cells constitutively express a wild-type RLIP76. The wild-type was removed by treating H358 cells with si-RNA directed at the region encoding aa 171-185, to silence the expression of wild-type RLIP76, while leaving the expression of 171-185 mutant unaffected. For this, a 23-nucleotide sequence motif comprising AA(N19)TT or NA(N21) (N, any nucleotide) with approximately 50% GC content was searched for. The sequence of sense si-RNA corresponds to N21. The 3' end of the sense si-RNA was converted to TT to generate a symmetric duplex with respect to the sequence composition of sense and antisense 3' overhangs. The selected si-RNA sequence was subjected to blast-search (NCBI database) against EST libraries, to ensure that only one gene was targeted. Chemically synthesized si-RNA duplex in the 2' de-protected and desalted forms, was purchased from Dharmacon. A 23-nucleotide long scrambled si-RNA duplex was used as a control. The scrambled si-RNA sequence was not homologous with RLIP76 mRNA in a blast-search against RLIP76. The targeted cDNA sequence was AAGAAAAAGCCAATTCAGGAGCC (SEQ ID NO:13) corresponding to nucleotides 508 to 528. The corresponding sense si-RNA sequence was GAAAAAGCCAA-UUCAGGAGCCdTdT (SEQ ID NO: 14) and the antisense si-RNA sequence was GGCUCCUGAAUUGGCU-UUUUCdTdT (SEQ ID NO: 15). The sequences of the scrambled si-RNA in the sense and antisense directions were GUAACUGCAACGAUUUCGAUGdTdT (SEQ ID NO: 16) and CAUCGAAAUCGUUGCAGUUACdTdT (SEQ ID NO: 17), respectively.

Transfection of si-RNA duplexes was performed using a kit (Transmessenger Transfection Reagent Kit from Qiagen) and assayed for expression about 24 hours later. Cells (approximately $3\times10^6$) were placed into six-well plates and after about 24 hours were incubated for about 3 hours with RLIP76 si-RNA or scrambled si-RNA in an appropriate transfection reagent. Excess si-RNA was washed off with PBS and medium was added. Cell samples were pelleted, solubilized in a lysis buffer (10 mM Tris-HCl, pH 7.4, containing 1.4 mM β-mercaptoethanol, 100 μM EDTA, 50 μM BHT, 100 μM PMSF and 1% polidocanol), sonicated and then incubated for about 4 h in the cold (4° C.). Afterwards, each sample was centrifuged and supernatants (containing both cytosolic proteins and solubilized membrane proteins) collected and analyzed by Western blot analyses according to a method provided by Towbin et al. (Towbin, et al. PNAS 1979; 76:4350-4353) using anti-RLIP76 IgG as well as IgG against the peptide 171-185. Gel bands were quantified by scanning densitometry. Polyclonal antibodies against various deleted epitope regions of RLIP76 were custom made. The peptide antibodies as well as pre-immune serum were purified by DE-52 anion exchange chromatography, followed by protein-A-Sepharose affinity chromatography to obtain pure IgG fractions. Immuno-reactivity and specificity of these peptides using their respective purified IgG were checked by dot blot analyses.

The si-RNA 171-185 effectively silenced wild-type RLIP76 expression in the untransfected, empty-vector-transfected, as well as wild-type RLIP76 transfected cells (data not shown; see Yadav et al., 2004). Antibodies against the 171-185 peptide failed to detect RLIP76 antigen, while antibodies against full-length RLIP76 recognized the persistent presence of the residual deletion mutant RLIP76. Western blotting against the anti-del 171-185 antibody showed no signal in the RLIP76 deletion mutant transfected cells confirming that expression of wild-type RLIP76 was effectively blocked in these cells. Cell surface expression of RLIP76 in del 171-185 transfected cells with or without pre-treatment with si-RNA directed at aa 171-185 using immunohistochemical analysis and an anti-del 171-185 antibody showed that cells with control si-RNA had significant cell surface signal which was absent in cells in which RLIP had been silenced by the si-RNA. RLIP76 is, thus, an integral membrane protein with at least one cell surface domain spanning amino acids 154 to 219.

Accordingly, the present invention provides several surface epitope regions of RLIP that, when altered, blocked or deleted, prevent RLIP from performing its transport function. Compositions of the present invention include the several surface epitope regions as well as use of these surface epitope regions to obtain specific inhibitors of RLIP that are capable of altering, inhibiting or the transport function of RLIP. The inhibitors include si-RNAs, each having a sequence directed against the one or more surface epitope regions as well as phosphorothioate antisense oligonucleotides directed against such surface epitope regions (e.g., GGCTCCTGAATTG-GCTTTTTC; SEQ ID NO:18) and a corresponding silencing RNA sequence to the phosphorothioate antisense oligonucleotides (e.g., AAGAAAAGCCAATTCAGGAGCC; SEQ ID NO: 19), where, SEQ ID NO: 19 corresponds with the targeted cDNA sequence for nucleotides 508 to 528 used to generate the antisense si-RNA or SEQ ID NO: 13. In addition, inhibitors include antibodies (monoclonal and/or polyclonal) directed against the one or more surface epitope regions, such regions including SEQ ID NO: 3 and SEQ ID NO:4. Moreover, the inhibitors identified herein provide compounds for anti-seizure medicines. Importantly, the inhibitors are additional targets for identifying important compounds and small molecule from chemical library screenings, wherein the identified compounds and/or small molecules are effective as anti-cancer medicines.

While particular embodiments of the invention and method steps of the invention have been described herein, additional alternatives not specifically disclosed but known in the art are intended to fall within the scope of the invention. Thus, it is understood that other embodiments and applications of the present invention will be apparent to those skilled in the art without departing from the scope and spirit of the appended claims and drawings.

The invention claimed is:

1. A method of inhibiting growth of a malignant cell expressing RLIP76 comprising contacting the cell expressing RLIP76 with a composition that inhibits expression of RLIP76, wherein the composition comprises a proteoliposome, and wherein the composition comprises an anti-sense nucleic acid or double stranded siRNA molecule that targets nucleotides encoding a region of RLIP76 selected from the group consisting of SEQ ID NO:3, and SEQ ID NO:4.

2. The method of claim 1, wherein the anti-sense nucleic acid is in a composition comprising a pharmaceutically acceptable carrier.

3. The method of claim 1, wherein the composition comprises a liposome anti-sense nucleic acid that has the nucleic acid sequence of SEQ ID NO:5.

4. The method of claim 1, wherein the malignant cell is a melanoma cell, a small cell lung cancer cell, a non-small cell lung cancer cell, an ovarian cancer cell, a prostate cancer cell or an adenocarcinoma cell.

5. The method of claim 1, wherein the malignant cell is a melanoma cell.

6. The method of claim 1, wherein the cell is in a subject.

7. The method of claim 1, wherein the cell is in a human subject.

8. A method of inhibiting growth of a malignant cell expressing RLIP76 in a subject comprising: administering to the subject a pharmaceutically acceptable composition comprising an effective amount of an anti-sense nucleic acid that is effective to inhibit expression of RLIP76 in the malignant cell, wherein the pharmaceutically acceptable composition comprises a liposome, and wherein the anti-sense nucleic acid targets nucleotides encoding a region of RLIP76 selected from the group consisting of SEQ ID NO:4, and SEQ ID NO:3.

9. The method of claim 8, wherein the anti-sense nucleic acid is complementary to an mRNA that encodes SEQ ID NO:22.

10. The method of claim 8, wherein the malignant cell is a melanoma cell, a small cell lung cancer cell, a non-small cell lung cancer cell, an ovarian cancer cell, a prostate cancer cell or an adenocarcinoma cell.

11. The method of claim 8, wherein the malignant cell is a melanoma cell.

* * * * *

UNITED STATES PATENT AND TRADEMARK OFFICE
CERTIFICATE OF CORRECTION

PATENT NO. : 8,586,553 B2
APPLICATION NO. : 12/055138
DATED : November 19, 2013
INVENTOR(S) : Sanjay Awasthi, Sharad S. Singhal and Sushma Yadav It is certified that error appears in the above-identified patent and that said Letters Patent is hereby corrected as shown below:

In the Specification:

Column 1, replace lines 18-25 with the following:

--STATEMENT AS TO RIGHTS TO INVENTIONS MADE UNDER FEDERALLY SPONSORED RESEARCH OR DEVELOPMENT

This invention was made with government support under CA 77495 awarded by the National Institutes of Health. The government has certain rights in this invention.--

Signed and Sealed this
Second Day of September, 2014

Michelle K. Lee
*Deputy Director of the United States Patent and Trademark Office*

UNITED STATES PATENT AND TRADEMARK OFFICE
CERTIFICATE OF CORRECTION

| | |
|---|---|
| PATENT NO. | : 8,586,553 B2 |
| APPLICATION NO. | : 12/055138 |
| DATED | : November 19, 2013 |
| INVENTOR(S) | : Awasthi et al. |

Page 1 of 1

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 808 days.

Signed and Sealed this
Twenty-first Day of April, 2015

Michelle K. Lee
*Director of the United States Patent and Trademark Office*